(12) United States Patent
Combs et al.

(10) Patent No.: US 10,227,359 B2
(45) Date of Patent: *Mar. 12, 2019

(54) TRICYCLIC HETEROCYCLES AS BET PROTEIN INHIBITORS

(71) Applicant: Incyte Corporation, Wilmington, DE (US)

(72) Inventors: Andrew P. Combs, Kennett Square, PA (US); Richard B. Sparks, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/802,142

(22) Filed: Nov. 2, 2017

(65) Prior Publication Data

US 2018/0222920 A1    Aug. 9, 2018

Related U.S. Application Data

(63) Continuation of application No. 15/356,002, filed on Nov. 18, 2016, now Pat. No. 9,834,565, which is a continuation of application No. 14/852,958, filed on Sep. 14, 2015, now Pat. No. 9,527,864.

(60) Provisional application No. 62/050,500, filed on Sep. 15, 2014.

(51) Int. Cl.
*C07D 498/06*    (2006.01)

(52) U.S. Cl.
CPC .................. *C07D 498/06* (2013.01)

(58) Field of Classification Search
CPC .................................................. C07D 498/06
USPC ....................................... 544/101; 514/230.2
See application file for complete search history.

(56) References Cited

U.S. PATENT DOCUMENTS

| | | | |
|---|---|---|---|
| 5,589,476 A | 12/1996 | Jegham et al. | |
| 8,633,186 B2 | 1/2014 | Tachdjian et al. | |
| 8,669,249 B2 | 3/2014 | Brown et al. | |
| 9,012,642 B2 | 4/2015 | Haydar et al. | |
| 9,227,985 B2 | 1/2016 | Combs et al. | |
| 9,290,514 B2 | 3/2016 | Combs et al. | |
| 9,309,246 B2 | 4/2016 | Rodgers et al. | |
| 9,315,501 B2 | 4/2016 | Yue et al. | |
| 9,399,640 B2 | 7/2016 | Yue et al. | |
| 9,527,864 B2 * | 12/2016 | Combs ................ | C07D 498/06 |
| 9,533,997 B2 | 1/2017 | Combs et al. | |
| 9,540,368 B2 | 1/2017 | Combs et al. | |
| 9,624,241 B2 | 4/2017 | Combs et al. | |
| 9,737,516 B2 | 8/2017 | Yue et al. | |
| 9,777,003 B2 | 10/2017 | Shepard et al. | |
| 9,834,565 B2 | 12/2017 | Combs et al. | |
| 9,850,257 B2 | 12/2017 | Combs et al. | |
| 9,918,990 B2 | 3/2018 | Yue et al. | |
| 9,938,294 B2 | 4/2018 | Combs et al. | |
| 9,957,628 B2 | 5/2018 | Combs et al. | |
| 2002/0004510 A1 | 1/2002 | McCall et al. | |
| 2007/0191447 A1 | 8/2007 | Kodo et al. | |
| 2007/0244096 A1 | 10/2007 | Fox et al. | |
| 2008/0306093 A1 | 12/2008 | Servant et al. | |
| 2009/0306122 A1 | 12/2009 | Staehle et al. | |
| 2013/0045229 A1 | 2/2013 | Iadonato et al. | |
| 2013/0261109 A1 | 10/2013 | Miyoshi et al. | |
| 2013/0281396 A1 | 10/2013 | McLure et al. | |
| 2013/0281397 A1 | 10/2013 | McLure et al. | |
| 2013/0281398 A1 | 10/2013 | McLure et al. | |
| 2013/0281399 A1 | 10/2013 | McLure et al. | |
| 2014/0135316 A1 | 5/2014 | Albrecht et al. | |
| 2014/0275030 A1 | 9/2014 | Combs et al. | |
| 2015/0011540 A1 | 1/2015 | Combs et al. | |
| 2015/0148342 A1 | 5/2015 | Yue et al. | |
| 2015/0148372 A1 | 5/2015 | Yue et al. | |
| 2015/0148375 A1 | 5/2015 | Yue et al. | |
| 2015/0175604 A1 | 6/2015 | Rodgers et al. | |
| 2015/0307493 A1 | 10/2015 | Combs et al. | |
| 2016/0046650 A1 | 2/2016 | Combs et al. | |
| 2016/0075721 A1 | 3/2016 | Combs et al. | |
| 2016/0159817 A1 | 6/2016 | Combs et al. | |
| 2016/0168148 A1 | 6/2016 | Shepard | |
| 2016/0213654 A1 | 7/2016 | Yue et al. | |
| 2016/0331749 A1 | 11/2016 | Bogdan et al. | |
| 2017/0014418 A1 | 1/2017 | Yue et al. | |
| 2017/0121347 A1 | 5/2017 | Chen et al. | |
| 2017/0158689 A1 | 6/2017 | Combs et al. | |
| 2017/0158710 A1 | 6/2017 | Combs et al. | |
| 2017/0210754 A1 | 7/2017 | Combs et al. | |
| 2017/0127985 A1 | 8/2017 | Combs et al. | |
| 2017/0362229 A1 | 12/2017 | Chen et al. | |

FOREIGN PATENT DOCUMENTS

| | | |
|---|---|---|
| CA | 2171579 | 9/1996 |
| EP | 0646583 | 4/1995 |
| EP | 0 732 334 | 9/1996 |

(Continued)

OTHER PUBLICATIONS

Ai et al., "Signal-induced Brd4 release from chromatin is essential for its role transition from chromatin targeting to transcriptional regulation," Nucleic Acids Res., 2011, 1-13.

Bamborough et al., "Fragment-Based Discovery of Bromodomain Inhibitors Part 2: Optimization of Phenylisoxazole Sulfonamides," J Med Chem., 2012, 55:587-596.

(Continued)

*Primary Examiner* — Kahsay Habte
(74) *Attorney, Agent, or Firm* — Fish & Richardson P.C.

(57) ABSTRACT

The present disclosure relates to tricyclic heterocycles which are inhibitors of BET proteins such as BRD2, BRD3, BRD4, and BRD-t and are useful in the treatment of diseases such as cancer.

6 Claims, No Drawings

(56) References Cited

FOREIGN PATENT DOCUMENTS

| | | |
|---|---|---|
| EP | 1462103 | 9/2004 |
| EP | 2 239 264 | 10/2010 |
| EP | 2415767 | 2/2012 |
| EP | 2568287 | 3/2013 |
| EP | 2573559 | 3/2013 |
| FR | 2747678 | 10/1997 |
| JP | H 03014566 | 1/1991 |
| JP | H 05-097849 | 4/1993 |
| JP | 08-269058 | 10/1996 |
| JP | 2004-502650 | 1/2004 |
| JP | 2006-509764 | 3/2006 |
| JP | 2008-532954 | 8/2008 |
| JP | 2009-503069 | 1/2009 |
| JP | 2012-529536 | 11/2012 |
| JP | 2012-530053 | 11/2012 |
| JP | 2013/010719 | 1/2013 |
| KR | 20150037711 | 4/2015 |
| WO | WO 2002/000196 | 1/2002 |
| WO | WO 2004/024736 | 3/2004 |
| WO | WO 2005/080334 | 9/2005 |
| WO | WO 2005/099688 | 10/2005 |
| WO | WO 2006/124874 | 11/2006 |
| WO | WO 2007/018998 | 2/2007 |
| WO | WO 2008/154221 | 12/2008 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/024987 | 3/2011 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/133722 | 10/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/107465 | 8/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | WO 2015/002754 | 1/2015 |
| WO | WO 2015/004533 | 1/2015 |
| WO | WO 2015/004534 | 1/2015 |
| WO | WO 2015/006193 | 1/2015 |
| WO | WO 2015/007711 | 1/2015 |
| WO | WO 2015/013635 | 1/2015 |
| WO | WO 2015/081203 | 6/2015 |
| WO | WO 2015/095445 | 6/2015 |
| WO | WO 2015/162169 | 10/2015 |
| WO | WO 2015/163485 | 10/2015 |
| WO | WO 2015/164480 | 10/2015 |
| WO | WO 2015/168555 | 11/2015 |
| WO | WO 2015/168621 | 11/2015 |
| WO | WO 2015/169951 | 11/2015 |
| WO | WO 2015/169953 | 11/2015 |
| WO | WO 2015/184257 | 12/2015 |
| WO | WO 2016/044130 | 3/2016 |
| WO | WO 2016/077378 | 5/2016 |
| WO | WO 2016/186453 | 11/2016 |
| WO | WO 2016/194806 | 12/2016 |
| WO | WO 2017/127930 | 8/2017 |
| WO | WO 2017/133681 | 8/2017 |

OTHER PUBLICATIONS

Bartholomeeusen et al., "BET bromodomain inhibition activates transcription via a transient release of P-TEFb from 7SK snRNP," JBC, 2012, 16 pages.

(56) References Cited

OTHER PUBLICATIONS

Bauer, "Pharmaceutical Solids—The Amorphous Phase," Journal of Validation Technology, Jan. 2009, 15(3): 63-68.
Belkina and Denis, "BET domain co-regulators in obesity inflammation and cancer," Nat Rev Cancer, Jul. 2012, 12:465-477.
Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Byrn et al., "Pharmaceutical Solids: A Strategic Approach to Regulatory Considerations," Pharmaceutical Research, Jul. 1995, 12(7): 945-954.
Caira, "Crystalline Polymorphism of Organic Compounds," Topics in Current Chemistry, 1998, 198: 163-208.
Cheng et al., "Inhibition of BET Bromodomain Targets Genetically Diverse Glioblastoma," Clin Cancer Res 19:1748-1759, Feb. 2013.
Chiang, "Brd4 engagement from chromatin targeting to transcriptional regulation: selective contact with acetylated histone H3 and H4," Biology Reports, Dec. 2009, 1:98, 7 pages.
Chilean Office Action in Chilean Application No. 201502734, dated Jan. 18, 2017, 8 pages (English Translation).
Chinese Office Action in Chinese Application No. 201480025137, dated May 17, 2016, 14 pages (English Translation).
Chinese Office Action in Chinese Application No. 201480025137, dated Feb. 16, 2017, 21 pages (w/ English Translation).
Chinese Office Action in Chinese Application No. 201480025137, dated Oct. 13, 2017, 7 pages (English Translation).
Chung et al., "Discovery and Characterization of Small Molecule Inhibitors of the BET Family Bromodomains," J Med Chem., 2011,54:3827-3838.
Chung et al., "Fragment-Based Discovery of Bromodomain Inhibitors Part 1: Inhibitor Binding Modes and Implications for Lead Discovery," J Med Chem., 2011, 11 pages.
Chung et al., "Fragment-based discovery of bromodomain inhibitors part 1: inhibitor binding modes and implications for lead discovery," Supporting Information, 2011, 6 pages.
Colombian Office Action in Colombian Application No. 15-227. 987, dated May 23, 2017, 5 pages.
Dawson et al., "Inhibition of BET recruitment to chromatin as an effective treatment for MLL-fusion leukaemia," Nature, 2011, 5 pages.
Dawson, "Supplementary Information: Inhibition of BET recruitment to chromatin as an effective treatment for MLL-fusion leukaemia," Nature, 2011, 50 pages.
Delmore et al., "BET bromodomain inhibition as a therapeutic strategy to target c-Myc," Cell, 2011, 146(6):904-917, Supplemental Information: S1-S11.
Delmore et al., "BET bromodomain inhibition as a therapeutic strategy to target c-Myc," Cell, Sep. 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Draker et al., "A Combination of H2A.Z and H4 Acetylation Recruits Brd2 to Chromatin during Transcriptional Activation," PLoS Genet., Nov. 2012, 8(11):e1003047, 17 pages.
Dorwald, F. Zaragoza. Side Reactions in Organic Synthesis: A Guide to Successful Synthesis Design, Weinheim: Wiley-VCH Verlag GmbH & Co. KGaA, 2005, Preface.

Eurasian Office Action in Eurasian Application No. 201692134, dated Jun. 6, 2017, 4 pages (English Translation).
Filippakopoulos and Knapp, "Targeting bromodomains: epigenetic readers of lysine acetylation," Nature Rev Drug Disc., May 2014, 13:337-356
Filippakopoulos et al., "Benzodiazepines and benzotriazepines as protein interaction inhibitors targeting bromodomains of the BET family," Bioorg Med Chem., 2011, 9 pages.
Filippakopoulos et al., "Histone Recognition and Large-Scale Structural Analysis of the Human Bromodomain Family," Cell, Mar. 2012, 149:214-231.
Filippakopoulos et al., "Selective inhibition of BET bromodomains," Nature, 2010, 468:1067-1073.
Filippakopoulos et al., "Supplemental Information: Selective inhibition of BET bromodomains," Nature, 2010, 468:1067-1073.
Floyd et al., "Supplemental Information: The bromodomain protein Brd4 insulates chromatin from DNA damage signalling," Nature, 2013, 14 pages.
Floyd et al., "The bromodomain protein Brd4 insulates chromatin from DNA damage signalling," Nature, 2013, 498:246-250.
French et al., "BRD4-NUT fusion oncogene: a novel mechanism in aggressive carcinoma," Cancer Res., 2003, 63(2):304-307.
French et al., "BRD-NUT oncoproteins: a family of closely related nuclear proteins that block epithelial differentiation and maintain the growth of carcinoma cells," Oncogene, 2008, 27:2237-2242.
French et al., "Midline carcinoma of children and young adults with NUT rearrangement," J Clin. Oneal., 2004, 22(20):4135-4139.
French, "Demystified molecular pathology of NUT midline carcinomas," J Clin Pathol., 2010, 63:492-496.
French, "NUT midline carcinoma," Cancer Genet Cytogenetics, 2010, 203:16-20.
Frizzo et al., "Structural and thermodynamic properties of new pyrazolo[3,4-d] pyridazinones," Thermochimica Acta., Oct. 2013, 574:63-72.
Gallenkamp et al., "Bromodomains and their Pharmacological Inhibitors," Chem Med Chem., Mar. 2014, 9(3):438-464.
Garnier et al., "BET bromodoma in inhibitors: a patent review," Exp Opin Therapeutic Patents, Feb. 2014, 24(2):185-199.
Greenwald et al., "Eμ-BRD2 transgenic mice develop B-cell lymphoma and leukemia," Blood 103(4):1475-1484, Feb. 2004.
Hackam et al., JAMA, 296(14), 2006, 1731-1732.
Hewings et al., "3,5-Dimethylisoxazoles Act As Acetyl-lysine-mimetic Bromodomain Ligands," J Med Chem., 2011, 54:6761-6770.
Hewings et al., "Progress in the Development and Applciation of Small Molecule Inhibitors of Bromodomain-Acetyl-lysine Interactions," J Med Chem., Nov. 2012, 104 pages (Author Manuscript).
Hewings et al., "Progress in the Development and Applciation of Small Molecule Inhibitors of Bromodomain-Acetyl-lysine Interactions," J Med Chem., Nov. 2012, 55(22):9393-9413.
Houzelstein et al., "Growth and Early Postimplantation Defects in Mice Deficient for the Bromodomain-Containing Protein Brd4," Mole Cell Biol., Jun. 2002, 22(11):3794-3802.
Huang et al., "Brd4 coactivates transcriptional activation of NF-κB via specific binding to acetylated RelA," Mol. Cell Biol., 2009, 29(5):1375-1387.
International Preliminary Report on Patentability in International Application No. PCT/US2014/045543, dated Jan. 21, 2016, 7 pages.
International Search Report and Written Opinion in International Application No. PCT/US2014/027872, dated Jun. 30, 2014, 12 pages.
International Search Report and Written Opinion in International Application No. PCT/US2014/045543, dated Sep. 10, 2014, 11 pages.
International Search Report and Written Opinion in International Application No. PCT/US2014/067598, dated Feb. 13, 2015, 9 pages.
International Search Report and Written Opinion in International Application No. PCT/US2014/067629, dated Feb. 16, 2015, 11 pages.
International Search Report and Written Opinion in International Application No. PCT/US2014/067691, dated Feb. 2, 2015, 10 pages.

(56) References Cited

OTHER PUBLICATIONS

International Search Report and Written Opinion in International Application No. PCT/US2014/071102, dated Feb. 13, 2015, 9 pages.
International Preliminary Report on Patentability in International Application No. PCT/US2014/027872, dated Sep. 24, 2015, 8 pages.
International Search Report and Written Opinion in International Application No. PCT/US2015/027047, dated Jul. 10, 2015, 14 pages.
International Search Report and Written Opinion in International Application No. PCT/US2015/049909, dated Dec. 7, 2015, 13 pages.
International Preliminary Report on Patentability in International Application No. PCT/US2014/067691, dated May 31, 2016, 7 pages.
International Preliminary Report on Patentability in International Application No. PCT/US2014/067629, dated May 31, 2016, 7 pages.
International Preliminary Report on Patentability in International Application No. PCT/US2014/067598, dated May 31, 2016, 7 pages.
International Preliminary Report on Patentability in International Application No. PCT/US2014/071102, dated Jun. 21, 2016, 7 pages.
International Preliminary Report on Patentability in International Application No. PCT/US2015/027047, dated Oct. 25, 2016, 10 pages.
International Search Report and Written Opinion in International Application No. PCT/US2016/059360, dated Feb. 13, 2017, 20 pages.
International Search Report and Written Opinion in International Application No. PCT/US2017/038121, dated Oct. 20, 2017, 20 pages.
Jang et al., "The bromodomain protein Brd4 is a positive regulatory component of P-TEFb and stimulates RNA polymerase II-dependent transcription," Mol. Cell, Aug. 2005, 19(4):523-534.
Japanese Office Action in Japanese Application No. 2016-502650, dated Jan. 10, 2017, 3 pages. (English translation only).
Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, Apr. 2008, 30(1):51-60.
Lockwood et al., "Sensitivity of human lung adenocarcinoma cell lines to targeted inhibition of BET epigenetic signaling proteins," PNAS Early Edition, 2012, 14 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, Is a BET Bromodomain Antagonist," PLOS ONE, Dec. 2013, 8(12):e83190, 12 pages.
Mertz et al., "Targeting MYC dependence in cancer by inhibiting BET bromodomains," PNAS, 2011, 108(40):16669-16674.

Mirguet et al., "From ApoA1 upregulation to BET family bromodomain inhibition: Discovery of I-BET151," Bioorg Med Chem Lett., 2012, 22:2963-2967.
Mochizuki et al., "The bromodomain protein Brd4 stimulates G1 gene transcription and promotes progression to S phase," J Biol. Chem. 2008, 283(14):9040-9048.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 Is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-Myc and IL7R in high-risk acute lymphoblastic leukemia," Blood, published online 2012, 29 pages.
Peturssion et al., "Protecting Groups in Carbohydrate Chemistry," J Chem. Educ., 1997, 74(11):1297-1303.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Puissant et al., "Targeting MYCN in Neuroblastoma by BET Bromodomain Inhibition," Cancer Discovery, 16 pages, Mar. 2013.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Ravin, "Preformulation," Remington's Pharmaceutical Sciences, 17th Ed., (Mack Publishing Company, Easton, 1985), pp. 1409-1423.
Sanchez and Zhou, "The role of human bromodomains in chromatin biology and gene transcription," Curr Opin Drug Discov Devel., Sep. 2009, 12(5):659-665 (Author Manuscript).
Shimamura et al., "Efficacy of BET Bromodomain Inhibition in Kras-Mutant Non-Small Cell Lung Cancer," Clin Cancer Res, 10 pages, 2013.
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Segura et al., "BRD4 Sustains Melanoma Proliferation and Represents a New Target for Epigenetic Therapy," Cancer Res 73:6264-6276, Aug. 2013.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy Number alterations of MYB in human cancer," Cell Cyle, Aug. 2010, 9(15):2986-2955.
Vidler et al., "Druggability Analysis and Structural Classification of Bromodomain Acetyl-lysine Binding Sites," J Med Chem., 2012, 14 pages.
Wang et al., "Brd2 disruption in mice causes severe obesity without Type 2 diabetes," Biochem. J., 2010, 425(1):71-83.
Wang et al., "The Bromodomain Protein Brd4 Associated with Acetylated Chromatin is Important for Maintenance of Higher-Order Chromatin Structure," JBC, 2012, 22 pages.

(56) References Cited

OTHER PUBLICATIONS

Weidner-Glunde et al., "What do viruses BET on?" Frontiers Biosci., Jan. 2010, 15:537-549.
Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Wyce et al., "Inhibition of BET bromodomain proteins as a therapeutic approach in prostate cancer,", Oncotarget, 13 pages, Nov. 2013.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Interaction of the bovine papillomavirus E2 protein with Brd4 tethers the viral DNA to host mitotic chromosomes," Cell, 2004, 117(3):349-60.
You et al., "Regulation of Aurora B Expression by the Bromodomain Protein Brd4," Mol Cell Biol., Sep. 2009, 29(18):5094-5103.
Zhang et al., "Bromodomain-Containing-Protein 4 (BRD4) Regulates RNA Polymerase II Serine 2 Phosphorylation in Human CD4+ T Cells," JBC, 2012, 30 pages.
Zhu et al., "Reactivation of latent HIV-1 by inhibition of BRD4," Cell Reports, 2012, 2(4):807-816.
Zuber et al., "An integrated approach to dissecting oncogene addiction implicates a Myb-coordinated self-renewal program as essential for leukemia maintenance," Genes Dev., 2011, 25:1628-1640.
Zuber et al., "RNAi screen identifies Brd4 as a therapeutic target in acute myeloid leukaemia," Nature, 2011, 478(7370):524-528.
Zuber et al., "Supplemental Information: RNAi screen identifies Brd4 as a therapeutic target in acute myeloid leukaemia," Nature, 2011, 33 pages.
Australian Office Action in Australian Application No. 2014228175, dated May 10, 2018, 4 pages.
Australian Office Action in Australian Application No. 2015249810, Aug. 21, 2018, 4 pages.
Colombian Office Action in Colombian Application No. NC2016/0003978, dated Jul. 16, 2018, 7 pages.
Indonesian Office Action P-00201506648, dated May 7, 2018, 5 pages. (english translation).
Philippian Office Action in Philippian application No. 1/2016/502115, dated Sep. 6, 2018, 4 pages.
Ukrainian Office Action in Ukrainian Application No. A201510087, dated Aug. 9, 2018, 69 pages.
Japanese Office Action in Japanese Application No. 2016-525398 , dated May 15, 2018, 5 pages. (English Translation).
Japanese Office Action in Japanese Application No. 2017-134538, dated Jun. 12, 2018, 7 pages. (English Translation).

* cited by examiner

TRICYCLIC HETEROCYCLES AS BET PROTEIN INHIBITORS

FIELD OF THE INVENTION

The present disclosure relates to tricyclic heterocycles which are inhibitors of BET proteins such as BRD2, BRD3, BRD4, and BRD-t and are useful in the treatment of diseases such as cancer.

BACKGROUND

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitously expressed while BRDt is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle (Mochizuki J Biol. Chem. 2008 283:9040-9048). BRD4 is essential for recruiting the protein translational elongation factor B complex to the promoters of inducible genes resulting in the phosphorylation of RNA polymerase II and stimulating productive gene transcription and elongation (Jang et al. Mol. Cell 2005 19:523-534). In some instances, a kinase activity of BRD4 may directly phosphorylate and activate RNA polymerase II (Devaiah et al. PNAS 2012 109:6927-6932). Cells lacking BRD4 show impaired progression through cell cycle. BRD2 and BRD3 are reported to associate with histones along actively transcribed genes and may be involved in facilitating transcriptional elongation (Leroy et al, Mol. Cell. 2008 30:51-60). In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation (Huang et al, Mol. Cell. Biol. 2009 29:1375-1387; Lamonica Proc. Nat. Acad. Sci. 2011 108:E159-168).

A recurrent translocation involving NUT (nuclear protein in testes) with BRD3 or BRD4 to form a novel fusion oncogene, BRD-NUT, is found in a highly malignant form of epithelial neoplasia (French et al, Cancer Research 2003 63:304-307; French et al, Journal of Clinical Oncology 2004 22:4135-4139). Selective ablation of this oncogene restores normal cellular differentiation and reverses the tumorigenic phenotype (Filippakopoulos et al, Nature 2010 468:1068-1073). Genetic knockdown of BRD2, BRD3 and BRD4 has been shown to impair the growth and viability of a wide range of hematological and solid tumor cells (Zuber et al, Nature 2011 478:524-528; Delmore et al, Cell 2011 146: 904-917). Aside from a role in cancer, BET proteins regulate inflammatory responses to bacterial challenge, and a BRD2 hypomorph mouse model showed dramatically lower levels of inflammatory cytokines and protection from obesity induced diabetes (Wang et al Biochem J. 2009 425:71-83; Belkina et al. J. Immunol 2013). In addition, some viruses make use of these BET proteins to tether their genomes to the host cell chromatin, as part of the process of viral replication or use BET proteins to facilitate viral gene transcription and repression (You et al, Cell 2004 117:349-60; Zhu et al, Cell Reports 2012 2:807-816).

Accordingly, there is a need for compounds that modulate the activity of the BET family of proteins, including BRD2, BRD3, and BRD4, that can be used to treat BET protein-associated diseases such as cancer. The compounds of the invention help meet this need.

SUMMARY

The present invention relates to, inter alia, an inhibitor of a BET protein, or a pharmaceutically acceptable salt thereof, wherein the inhibitor is a compound of Formula I:

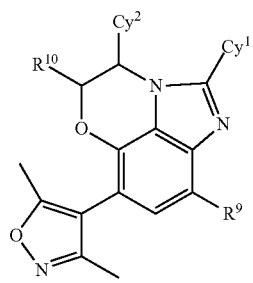

I

The present invention further relates to a pharmaceutical composition comprising a compound of Formula I, or a pharmaceutically acceptable salt thereof, and at least one pharmaceutically acceptable carrier.

The present invention further relates to a method of treating a disease or condition that is associated with a BET protein, comprising administering to a patient in need of such treatment a therapeutically effective amount of a compound of Formula I, or a pharmaceutically acceptable salt thereof.

The present invention further relates to a method of treating a disease or condition that is associated with a BET protein, comprising administering to said patient in need of such treatment a pharmaceutical composition comprising a compound of Formula I, or a pharmaceutically acceptable salt thereof, and pharmaceutically acceptable carrier.

The present invention further relates to a method of inhibiting a BET protein in a patient in need thereof, comprising administering to said patient a therapeutically effective amount of a compound of Formula I, or a pharmaceutically acceptable salt thereof.

The present invention further relates to a method of inhibiting a BET protein in a patient in need thereof, comprising administering to said patient a pharmaceutical composition comprising a compound of Formula I, or a pharmaceutically acceptable salt thereof, and pharmaceutically acceptable carrier.

The present invention further relates to a method of modulating the activity of a BET protein in a patient in need thereof, comprising administering to said patient a therapeutically effective amount of a compound of Formula I, or a pharmaceutically acceptable salt thereof.

The present invention further relates to a method of modulating the activity of a BET protein in a patient in need thereof, comprising administering to said patient a pharmaceutical composition comprising a compound of Formula I, or a pharmaceutically acceptable salt thereof, and pharmaceutically acceptable carrier.

The details of one or more embodiments are set forth in the description below. Other features, objects, and advantages will be apparent from the description and from the claims.

DETAILED DESCRIPTION

I. Compounds

The present invention relates to, inter alia, an inhibitor of a BET protein, wherein the inhibitor is a compound of Formula I:

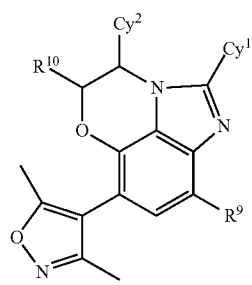

or a pharmaceutically acceptable salt thereof, wherein:
Cy$^1$ is a group of Formula Cy$^1$-A or Cy$^1$-B:

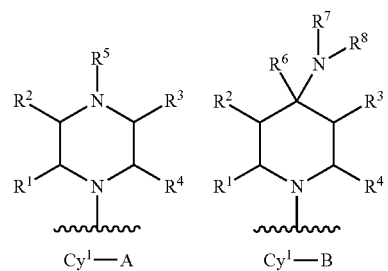

$R^1$, $R^2$, $R^3$, and $R^4$ are each independently selected from H and $C_{1-4}$ alkyl; or $R^2$ and $R^4$ are combined to form a bridging —CH$_2$— or —CH$_2$CH$_2$— group;

$R^5$ is —C(=O)R$^{5a}$, —C(=O)OR$^{5a}$, —C(=O)NR$^{5a}$R$^{5b}$, —S(=O)$_2$R$^{5a}$, or —S(=O)$_2$NR$^{5a}$R$^{5b}$;

$R^{5a}$ is $C_{1-4}$ alkyl, $C_{1-4}$ haloalkyl, $C_{1-4}$ hydroxyalkyl, ($C_{1-4}$ alkoxy)-$C_{1-4}$ alkyl-, $C_{3-6}$ cycloalkyl, or $C_{3-6}$ cycloalkyl-$C_{1-4}$ alkyl-;

$R^{5b}$ is H or $C_{1-4}$ alkyl;

$R^6$ is H or methyl;

$R^7$ is H, $C_{1-4}$ alkyl, —C(=O)R$^{7a}$, —C(=O)OR$^{7a}$, —C(=O)NR$^{7a}$R$^{7b}$, —S(=O)$_2$R$^{7a}$, or —S(=O)$_2$NR$^{7a}$R$^{7b}$;

$R^{7a}$ is $C_{1-4}$ alkyl, $C_{1-4}$ haloalkyl, $C_{1-4}$ hydroxyalkyl, ($C_{1-4}$ alkoxy)-$C_{1-4}$ alkyl-, $C_{3-6}$ cycloalkyl, or $C_{3-6}$ cycloalkyl-$C_{1-4}$ alkyl-;

$R^{7b}$ is H or $C_{1-4}$ alkyl;

$R^8$ is H or methyl;

Cy$^2$ is pyridin-2-yl or pyridin-3-yl, each of which is optionally substituted by F or Cl, wherein said F and Cl are meta or para to the pyridine nitrogen;

$R^9$ is H, F, or CH$_2$OH; and $R^{10}$ is H, —C(=O)NHCH$_3$, —C(=O)NHCH$_2$CH$_3$, —C(=O)NHCH$_2$CH$_2$CH$_3$, or —C(=O)NHCH(CH$_3$)$_2$;

provided:
i) when $R^{5a}$ is methyl, ethyl or i-propyl, then one of $R^1$, $R^2$, $R^3$, and $R^4$ is other than H;
ii) when $R^{7a}$ is methyl, ethyl, i-propyl, —CF$_3$, or methoxymethyl, then one of $R^1$, $R^2$, $R^3$, and $R^4$ is other than H; and
iii) when $R^7$ and $R^8$ are both methyl, then one of $R^1$, $R^2$, $R^3$, and $R^4$ is other than H.

In some embodiments, the compound is a compound of Formula Ia:

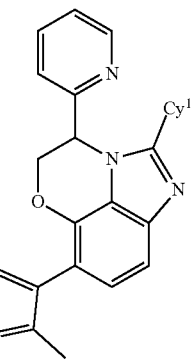

or a pharmaceutically acceptable salt thereof, wherein:
$Cy^1$ is a group of Formula $Cy^1$-A or $Cy^1$-B:

[Chemical structures of $Cy^1$—A and $Cy^1$—B shown]

$R^1$, $R^2$, $R^3$, and $R^4$ are each independently selected from H and $C_{1-4}$ alkyl;
or $R^2$ and $R^4$ are combined to form a bridging —$CH_2$— or —$CH_2CH_2$— group;
$R^5$ is —C(=O)$R^{5a}$, —C(=O)O$R^{5a}$, —C(=O)N$R^{5a}R^{5b}$, —S(=O)$_2R^{5a}$, or —S(=O)$_2$N$R^{5a}R^{5b}$;
$R^{5a}$ is $C_{1-4}$ alkyl, $C_{1-4}$ haloalkyl, $C_{1-4}$ hydroxyalkyl, ($C_{1-4}$ alkoxy)-$C_{1-4}$ alkyl-, $C_{3-6}$ cycloalkyl, or $C_{3-6}$ cycloalkyl-$C_{1-4}$ alkyl-;
$R^{5b}$ is H or $C_{1-4}$ alkyl;
$R^6$ is H or methyl;
$R^7$ is H, $C_{1-4}$ alkyl, —C(=O)$R^{7a}$, —C(=O)O$R^{7a}$, —C(=O)N$R^{7a}R^{7b}$, —S(=O)$_2R^{7a}$, or —S(=O)$_2$N$R^{7a}R^{7b}$;
$R^{7a}$ is $C_{1-4}$ alkyl, $C_{1-4}$ haloalkyl, $C_{1-4}$ hydroxyalkyl, ($C_{1-4}$ alkoxy)-$C_{1-4}$ alkyl-, $C_{3-6}$ cycloalkyl, or $C_{3-6}$ cycloalkyl-$C_{1-4}$ alkyl-;
$R^{7b}$ is H or $C_{1-4}$ alkyl; and
$R^8$ is H or methyl;
provided:
i) when $R^{5a}$ is methyl, ethyl or i-propyl, then one of $R^1$, $R^2$, $R^3$, and $R^4$ is other than H;
ii) when $R^{7a}$ is methyl, ethyl, i-propyl, —$CF_3$, or methoxymethyl, then one of $R^1$, $R^2$, $R^3$, and $R^4$ is other than H; and
iii) when $R^7$ and $R^8$ are both methyl, then one of $R^1$, $R^2$, $R^3$, and $R^4$ is other than H.

In some embodiments:
$Cy^1$ is a group of Formula $Cy^1$-A;
$R^1$, $R^2$, $R^3$, and $R^4$ are each independently selected from H and methyl;
or $R^2$ and $R^4$ are combined to form a bridging —$CH_2$— group;
$R^5$ is —C(=O)$R^{5a}$, —C(=O)O$R^{5a}$, —C(=O)N$R^{5a}R^{5b}$, —S(=O)$_2R^{5a}$, or —S(=O)$_2$N$R^{5a}R^{5b}$;
$R^{5a}$ is $C_{1-4}$ alkyl, $C_{1-4}$ haloalkyl, $C_{1-4}$ hydroxyalkyl, ($C_{1-4}$ alkoxy)-$C_{1-4}$ alkyl-, $C_{3-6}$ cycloalkyl, or $C_{3-6}$ cycloalkyl-$C_{1-4}$ alkyl-;
$R^{5b}$ is H or methyl;
provided when $R^{5a}$ is methyl, ethyl or i-propyl, then one of $R^1$, $R^2$, $R^3$, and $R^4$ is other than H.

In some embodiments:
$Cy^1$ is a group of Formula $Cy^1$-A;
$R^1$, $R^2$, $R^3$, and $R^4$ are each independently selected from H and methyl;
or $R^2$ and $R^4$ are combined to form a bridging —$CH_2$— group;
$R^5$ is —C(=O)$R^{5a}$; and
$R^{5a}$ is methyl, ethyl, n-propyl, i-propyl, n-butyl, i-butyl, s-butyl, t-butyl, trifluoromethyl, difluoromethyl, monofluoromethyl, trifluoroethyl, difluoroethyl, monofluoroethyl, hydroxyethyl, methoxymethyl, methoxyethyl, cyclopropyl, cyclobutyl, cyclopentyl, cyclohexyl, cyclopropylmethyl, cyclobutylmethyl, cyclopentylmethyl, or cyclohexylmethyl.

In some embodiments, $R^5$ is —C(=O)$R^{5a}$.
In some embodiments, $R^5$ is —C(=O)N$R^{5a}R^{5b}$.
In some embodiments, $R^5$ is —S(=O)$_2R^{5a}$.
In some embodiments, $R^{5a}$ is methyl, ethyl, n-propyl, i-propyl, n-butyl, i-butyl, s-butyl, t-butyl, trifluoromethyl, difluoromethyl, monofluoromethyl, trifluoroethyl, difluoroethyl, monofluoroethyl, hydroxyethyl, methoxymethyl, methoxyethyl, cyclopropyl, cyclobutyl, cyclopentyl, cyclohexyl, cyclopropylmethyl, cyclobutylmethyl, cyclopentylmethyl, or cyclohexylmethyl.
In some embodiments, $R^{5a}$ is n-propyl, n-butyl, i-butyl, s-butyl, t-butyl, trifluoromethyl, difluoromethyl, monofluoromethyl, trifluoroethyl, difluoroethyl, monofluoroethyl, hydroxyethyl, methoxymethyl, methoxyethyl, cyclopropyl, cyclobutyl, cyclopentyl, cyclohexyl, cyclopropylmethyl, cyclobutylmethyl, cyclopentylmethyl, or cyclohexylmethyl.
In some embodiments, $R^{5a}$ is methyl, ethyl, n-propyl, i-propyl, n-butyl, i-butyl, s-butyl, t-butyl, methoxymethyl, methoxyethyl, cyclopropyl, cyclobutyl, cyclopentyl, or cyclohexyl.
In some embodiments, $R^{5a}$ is n-propyl, n-butyl, i-butyl, s-butyl, t-butyl, methoxymethyl, methoxyethyl, cyclopropyl, cyclobutyl, cyclopentyl, or cyclohexyl.
In some embodiments, $R^{5a}$ is methyl, ethyl, n-propyl, i-propyl, t-butyl, methoxymethyl, cyclopropyl, or cyclobutyl.
In some embodiments, $R^{5a}$ is n-propyl, t-butyl, methoxymethyl, cyclopropyl, or cyclobutyl. In some embodiments, $R^{5a}$ is n-propyl. In some embodiments, $R^{5a}$ is t-butyl.
In some embodiments, $R^{5a}$ is methoxymethyl. In some embodiments, $R^{5a}$ is cyclopropyl.
In some embodiments, $R^{5a}$ is cyclobutyl.
In some embodiments:
$Cy^1$ is a group of Formula $Cy^1$-B;
$R^1$, $R^2$, $R^3$, and $R^4$ are each independently selected from H and methyl;
or $R^2$ and $R^4$ are combined to form a bridging —$CH_2$— group;
$R^6$ is H or methyl;
$R^7$ is H, $C_{1-4}$ alkyl, —C(=O)$R^{7a}$, —C(=O)O$R^{7a}$, —C(=O)N$R^{7a}R^{7b}$, —S(=O)$_2R^{7a}$, or —S(=O)$_2$N$R^{7a}R^{7b}$;
$R^{7a}$ is $C_{1-4}$ alkyl, $C_{1-4}$ haloalkyl, $C_{1-4}$ hydroxyalkyl, ($C_{1-4}$ alkoxy)-$C_{1-4}$ alkyl-, $C_{3-6}$ cycloalkyl, or $C_{3-6}$ cycloalkyl-$C_{1-4}$ alkyl-;
$R^{7b}$ is H or methyl; and
$R^8$ is H or methyl;
provided: when $R^{7a}$ is methyl, ethyl, i-propyl, —$CF_3$, or methoxymethyl, then one of $R^1$, $R^2$, $R^3$, and $R^4$ is other than H; and when $R^7$ and $R^8$ are both methyl, then one of $R^1$, $R^2$, $R^3$, and $R^4$ is other than H.

In some embodiments:
$Cy^1$ is a group of Formula $Cy^1$-B;
$R^1$, $R^2$, $R^3$, and $R^4$ are each independently selected from H and methyl;
or $R^2$ and $R^4$ are combined to form a bridging —$CH_2$— group;
$R^6$ is H or methyl;
$R^7$ is —C(=O)$R^{7a}$, —C(=O)N$R^{7a}R^{7b}$, or —S(=O)$_2R^{7a}$;
$R^{7a}$ is methyl, ethyl, n-propyl, i-propyl, n-butyl, i-butyl, s-butyl, t-butyl, trifluoromethyl, difluoromethyl, monofluoromethyl, trifluoroethyl, difluoroethyl, monofluoroethyl, hydroxyethyl, methoxymethyl, methoxyethyl, cyclopropyl, cyclobutyl, cyclopentyl, cyclohexyl, cyclopropylmethyl, cyclobutylmethyl, cyclopentylmethyl, or cyclohexylmethyl;
$R^{7b}$ is H or methyl; and
$R^8$ is H or methyl.

In some embodiments, $R^7$ is -C(=O)$R^{7a}$, —C(=O)N$R^{7a}R^{7b}$, or —S(=O)$_2R^{7a}$.

In some embodiments, $R^7$ is -C(=O)$R^{7a}$.

In some embodiments, $R^{7a}$ is methyl, ethyl, n-propyl, i-propyl, n-butyl, i-butyl, s-butyl, t-butyl, trifluoromethyl, difluoromethyl, monofluoromethyl, trifluoroethyl, difluoroethyl, monofluoroethyl, hydroxyethyl, methoxymethyl, methoxyethyl, cyclopropyl, cyclobutyl, cyclopentyl, cyclohexyl, cyclopropylmethyl, cyclobutylmethyl, cyclopentylmethyl, or cyclohexylmethyl.

In some embodiments, $R^{7a}$ is n-propyl, n-butyl, i-butyl, s-butyl, t-butyl, difluoromethyl, monofluoromethyl, trifluoroethyl, difluoroethyl, monofluoroethyl, hydroxyethyl, methoxyethyl, cyclopropyl, cyclobutyl, cyclopentyl, cyclohexyl, cyclopropylmethyl, cyclobutylmethyl, cyclopentylmethyl, or cyclohexylmethyl.

In some embodiments, $R^{7a}$ is methyl, ethyl, n-propyl, i-propyl, n-butyl, i-butyl, s-butyl, t-butyl, methoxymethyl, methoxyethyl, cyclopropyl, cyclobutyl, cyclopentyl, or cyclohexyl.

In some embodiments, $R^{7a}$ is n-propyl, n-butyl, i-butyl, s-butyl, t-butyl, cyclopropyl, cyclobutyl, cyclopentyl, or cyclohexyl.

In some embodiments, $R^{7a}$ is methyl, ethyl, n-propyl, i-propyl, t-butyl, cyclopropyl, or cyclobutyl.

In some embodiments, $R^{7a}$ is n-propyl, t-butyl, cyclopropyl, or cyclobutyl.

In some embodiments, $R^{7a}$ is methyl.
In some embodiments, $R^{7a}$ is ethyl.
In some embodiments, $R^{7a}$ is n-propyl.
In some embodiments, $R^{7a}$ is i-propyl.
In some embodiments, $R^{7a}$ is t-butyl.
In some embodiments, $R^{7a}$ is cyclopropyl.
In some embodiments, $R^{7a}$ is cyclobutyl.
In some embodiments, $R^{7b}$ is H.
In some embodiments, $R^{7b}$ is methyl.
In some embodiments, $R^6$ is H.
In some embodiments, $R^6$ is methyl.

In some embodiments, $R^1$, $R^2$, $R^3$, and $R^4$ are each independently selected from H and methyl; or $R^2$ and $R^4$ are combined to form a bridging —CH$_2$— group.

In some embodiments, $R^1$, $R^2$, $R^3$, and $R^4$ are each independently selected from H and methyl.

In some embodiments, one substituent of $R^1$, $R^2$, $R^3$, and $R^4$ is methyl and the other three substituents are each independently H. In some embodiments, $R^1$ is methyl and $R^2$, $R^3$, and $R^4$ are each independently H. In some embodiments, $R^2$ is methyl and $R^1$, $R^3$, and $R^4$ are each independently H.

In some embodiments, two substituents of $R^1$, $R^2$, $R^3$, and $R^4$ are methyl and the other three substituents are each independently H. In some embodiments, $R^1$ and $R^4$ are each independently methyl and $R^2$ and $R^3$ are each independently H.

In some embodiments, each of $R^1$, $R^2$, $R^3$, and $R^4$ is H.

In some embodiments, $R^9$ is H. In some embodiments, $R^9$ is F. In some embodiments, $R^9$ is CH$_2$OH.

In some embodiments, $R^{10}$ is H.

In some embodiments, Cy$^2$ is pyridin-2-yl optionally substituted by F or Cl, wherein said F and Cl are meta or para to the pyridine nitrogen.

In some embodiments, Cy$^2$ is pyridin-2-yl.

In some embodiments, Cy$^2$ is pyridin-3-yl optionally substituted by F or Cl, wherein said F and Cl are meta or para to the pyridine nitrogen.

In some embodiments, Cy$^2$ is pyridin-3-yl.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "substituted" means that an atom or group of atoms formally replaces hydrogen as a "substituent" attached to another group. The hydrogen atom is formally removed and replaced by a substituent. A single divalent substituent, e.g., oxo, can replace two hydrogen atoms. The term "optionally substituted" means unsubstituted or substituted. The substituents are independently selected, and substitution may be at any chemically accessible position. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like. Where $C_{n-m}$ occurs more than once in a term, the values for each n and each m can be the same or different.

As used herein, the term "$C_{n-m}$ alkyl," employed alone or in combination with other terms, refers to a saturated hydrocarbon group that may be straight-chain or branched, having n to m carbons. In some embodiments, the alkyl group contains from 1 to 4 carbon atoms or from 1 to 3 carbon atoms, or from 1 to 2 carbon atoms. Examples of alkyl moieties include, but are not limited to, chemical groups such as methyl, ethyl, n-propyl, isopropyl, n-butyl, i-butyl, s-butyl, and t-butyl.

As used herein, the term "$C_{n-m}$ hydroxyalkyl," employed alone or in combination with other terms, refers to an alkyl group substituted by a hydroxy group. Example hydroxyalkyl groups include hydroxymethyl and hydroxyethyl.

As used herein, the term "$C_{n-m}$ alkoxy," employed alone or in combination with other terms, refers to a group of formula —O-alkyl, wherein the alkyl group has n to m carbons. Example alkoxy groups include methoxy, ethoxy, and propoxy (e.g., n-propoxy and isopropoxy). In some embodiments, the alkyl group has 1 to 4 carbon atoms. In some embodiments, the alkyl group has 1 to 3 carbon atoms. In some embodiments, the alkyl group has 1 to 2 carbon atoms. In some embodiments, the alkyl group has 1 to 3 carbon atoms. In some embodiments, the alkoxy group is methoxy.

As used herein, the term "($C_{n-m}$ alkoxy)-$C_{n-m}$ alkyl-," employed alone or in combination with other terms, refers to a $C_{n-m}$ alkyl group substituted by a $C_{n-m}$ alkoxy group. Example alkoxyalkyl groups include methoxymethyl, methoxyethyl, and ethoxymethyl.

As used herein, the term "cycloalkyl," employed alone or in combination with other terms, refers to a non-aromatic cyclic hydrocarbon moiety, which may optionally contain one or more alkenylene groups as part of the ring structure. One or more ring-forming carbon atoms of a cycloalkyl group can be oxidized to form carbonyl linkages.

In some embodiments, cycloalkyl is $C_{3-6}$ cycloalkyl. Exemplary cycloalkyl groups include cyclopropyl, cyclobutyl, cyclopentyl, cyclohexyl, cyclopentenyl, cyclohexenyl, cyclohexadienyl, and the like. In some embodiments, the cycloalkyl group is cyclopropyl, cyclobutyl, cyclopentyl, or cyclohexyl. In some embodiments, the cycloalkyl group is cyclopropyl or cyclobutyl. In some embodiments, the cycloalkyl group is cyclobutyl. In some embodiments, the cycloalkyl group is cyclopropyl.

As used herein, the term "cycloalkylalkyl," employed alone or in combination with other terms, refers to an alkyl group substituted by a cycloalkyl group. In some embodiments, cycloalkylalkyl is $C_{3-6}$ cycloalkyl-$C_{1-4}$ alkyl. In some embodiments, cycloalkylalkyl is $C_{3-6}$ cycloalkyl-$C_{1-3}$ alkyl. In some embodiments, cycloalkylalkyl is $C_{3-6}$ cycloalkyl-methyl. In some embodiments, cycloalkylalkyl is cyclobutylmethyl. In some embodiments, cycloalkylalkyl is cyclopropylmethyl.

As used herein, the term "$C_{n-m}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 4, 1 to 3, or 1 to 2 carbon atoms.

When the compound described herein contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of ca-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17$^{th}$ Ed., (Mack Publishing Company, Easton, 1985), p. 1418, Berge et al., *J. Pharm. Sci.,* 1977, 66(1), 1-19, and in Stahl et al., *Handbook of Pharmaceutical Salts: Properties, Selection, and Use,* (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent).

II. Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups,* (Thieme, 2007); Robertson, *Protecting Group Chemistry,* (Oxford University Press, 2000); Smith et al., *March's Advanced Organic Chemistry: Reactions, Mechanisms, and Structure,* 6$^{th}$ Ed. (Wiley, 2007); Peturssion et al., "Protecting Groups in Carbohydrate Chemistry," *J. Chem. Educ.,* 1997, 74(11), 1297; and Wuts et al., *Protective Groups in Organic Synthesis,* 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LCMS Purification: Improved Compound Specific Method Optimization*" Karl F. Blom, Brian Glass, Richard Sparks, Andrew P. Combs *J. Combi. Chem.* 2004, 6(6), 874-883) and normal phase silica chromatography.

Compounds of Formula I can be formed as shown in Scheme I. The phenols (i) can be alkylated using standard alkylating conditions (e.g., Cy$^2$C(O)C(R$^{10}$))—X (ii), where X is a leaving group such as halo (e.g. Br, Cl, I) or mesylate, or using Mitsunobu conditions (e.g., (Cy$^2$C(O)C(R$^{10}$))—X, where X=OH (ii), DEAD, or Ph$_3$P) to afford ether derivatives (iii). Cyclization in situ or upon heating can afford imine (iv) which upon reduction of the nitro group (e.g., H$_2$ with Pd/C or Fe) provides amine (v). Compounds (v) can either be reacted with carbonyldiimidazole or phosgene to form a urea and then halogenated with N-chlorosuccinimide, N-bromosuccinimide or N-iodosuccinimide to give tricyclic halide (vi) where X=Cl, Br or I. Urea (vi) can be coupled to M-(3,5-dimethylisoxazole), where M is a boronic acid, boronic ester or an appropriately substituted metal, under standard Suzuki conditions or standard Stille conditions (e.g., in the presence of a palladium(0) catalyst, such as tetrakis(triphenylphosphine)palladium(0)) and a base (e.g., a bicarbonate or carbonate base) or standard Negishi conditions (e.g., in the presence of a palladium(0) catalyst, such as tetrakis(triphenylphosphine)palladium(0), to give (ix).

Alternatively, urea (vi) can be halogenated by treatment with POCl$_3$, and then treated with an amine (HNRR) to give (x) which can then be coupled to M-(3,5-dimethylisoxazole), where M is a boronic acid, boronic ester or an appropriately substituted metal (e.g., Cy$^1$-M is Cy$^1$-B(OH)$_2$, Cy$^1$-Sn(Bu)$_4$, or Zn-Cy$^1$), under standard Suzuki conditions or standard Stille conditions (e.g., in the presence of a palladium(0) catalyst, such as tetrakis(triphenylphosphine) palladium(0)) and a base (e.g., a bicarbonate or carbonate base) or standard Negishi conditions (e.g., in the presence of a palladium(0) catalyst, such as tetrakis(triphenylphosphine) palladium(0)), to give (xi).

Alternatively, urea (ix) can be halogenated upon treatment with POCl$_3$, and then treated with an amine (HNRR) to give (xi) where R$^5$=NRR or the chloride derivative can be coupled to M-Cy$^1$, where M is a boronic acid, boronic ester or an appropriately substituted metal, under standard Suzuki conditions or standard Stille conditions (e.g., in the presence of a palladium(0) catalyst, such as tetrakis(triphenylphosphine)palladium(O)) and a base (e.g., a bicarbonate or carbonate base) or standard Negishi conditions (e.g., in the presence of a palladium(0) catalyst, such as tetrakis(triphenylphosphine)palladium(0)), to give (xi).

Amino compound (v) can either be treated with an ortho-ester, such as $Cy^1C(OEt)_3$, or an aldehyde $Cy^1CHO$ and $NaHSO_3$ to give an intermediate which can be halogenated with N-chlorosuccinimide, N-bromosuccinimide or N-iodosuccinimide to give (x), where X=Cl, Br, or I, which can be further converted to compounds of the invention (xi) as described above.

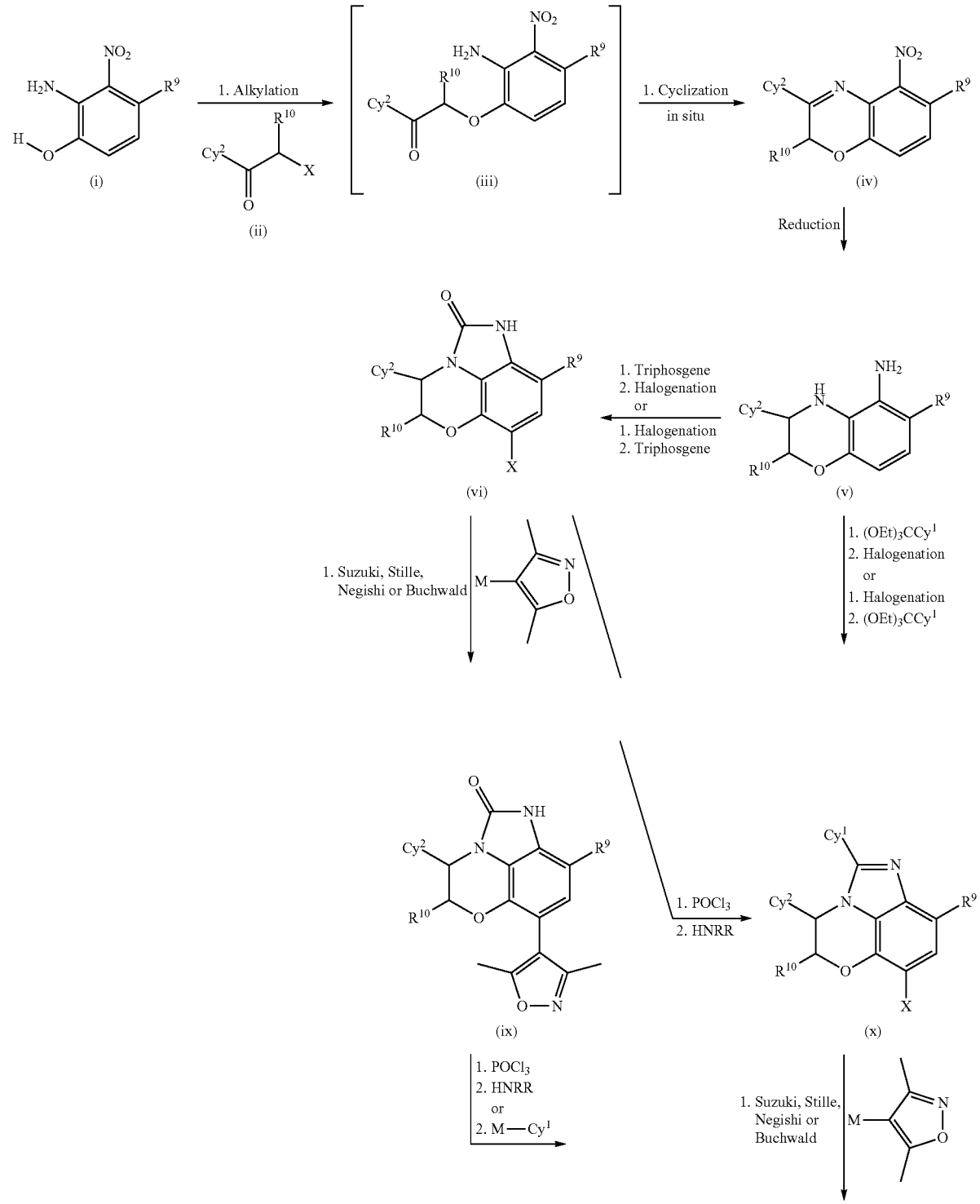

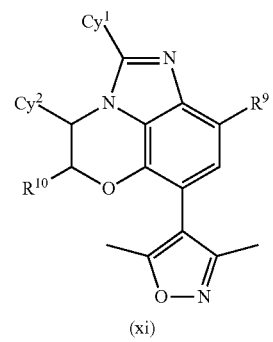

(xi)

For the synthesis of particular compounds, the general scheme described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

III. Methods of Use

The compounds of the invention can inhibit one or more of BET proteins BRD2, BRD3, BRD4, and BRD-t. In some embodiments, the compounds of the invention selectively inhibit one or more BET proteins over another. "Selective" means that the compound binds to or inhibits a BET protein with greater affinity or potency, respectively, compared to a reference, such as another BET protein. For example, the compounds can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compounds inhibit two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

The compounds of the invention are therefore useful for treating BET protein mediated disorders. The term "BET-mediated" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The compounds of the invention can therefore be used to treat or lessen the severity of diseases and conditions where BET proteins, such as BRD2, BRD3, BRD4, and/or BRD-t, or a mutant thereof, are known to play a role.

Diseases and conditions treatable using the compounds of the invention include, but are not limited to, cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a BET-mediated disease or disorder. Also provided is the use of a compound of the invention, or any of the embodiments thereof, or a pharmaceutical composition thereof, in the manufacture of a medicament for treating a BET-mediated disease or disorder.

Diseases that can be treated with the compounds of the invention include cancers. The cancers can include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, acute myeloid leukemia (AML), diffuse large B-cell lymphoma (DLBCL), ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor. In some embodiments, the cancer can be adult T-cell leukemia/lymphoma, Hodgkin's lymphoma, non-Hodgkin's lymphoma, leukemia, lymphoma, multiple myeloma, acute myeloid leukemia (AML), diffuse large B-cell lymphoma (DLBCL), primary central nervous system lymphoma, or T-cell lymphoma. In some embodiments, the cancer is Hodgkin's lymphoma. In some embodiments, the cancer is leukemia. In some embodiments, the cancer is lymphoma. In some embodiments, the cancer is T-cell lymphoma.

In some embodiments, the cancer is a hematological cancer.

In some embodiments, the cancer is multiple myeloma, acute myeloid leukemia (AML), or diffuse large B-cell lymphoma (DLBCL). In some embodiments, the cancer is multiple myeloma. In some embodiments, the cancer is acute myeloid leukemia (AML). In some embodiments, the cancer is diffuse large B-cell lymphoma (DLBCL).

The diseases treatable using the compounds of the invention also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with compounds of the invention also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the compounds of the invention also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the compounds of the invention also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Other diseases that can be treated with the compounds of the invention include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment, the compounds of the invention are indicated for the treatment of human papilloma virus infections of skin or cervical epithelia.

The diseases and conditions that can be treated with the compounds of the invention also include conditions that are associated with ischaemia-reperfusion injury. Examples of such conditions include, but are not limited to conditions such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The compounds of the invention are also useful in the treatment of disorders of lipid metabolism via the regulation of APO-A1 such as hypercholesterolemia, atherosclerosis and Alzheimer's disease.

The compounds of the invention are also useful in the treatment of fibrotic conditions such as idiopathic pulmonary fibrosis, renal fibrosis, post-operative stricture, keloid formation, scleroderma and cardiac fibrosis.

The compounds of the invention can also be used to treat ophthamological indications such as dry eye.

The compounds of the invention can also be used to treat heart disease such as heart failure.

The compounds of the invention can also be used to treat myelodysplastic syndrome (MDS).

As used herein, the term "contacting" refers to the bringing together of indicated moieties in an in vitro system or an in vivo system. For example, "contacting" a BET protein with a compound of the invention includes the administration of a compound of the present invention to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

For the terms "e.g." and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

IV. Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially. In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DEO11, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

In some embodiments, the compounds of the invention are administered in combination with a JAK kinase inhibitor (e.g., ruxolitinib, tofacitinib, baricitinib, CYT387, GLPG0634, lestaurtinib, pacritinib, TG101348, or a JAK1-selective inhibitor), a Pim kinase inhibitor (including inhibitors of one or more of PIM1, PIM2, and PIM3), a PI3 kinase inhibitor including PI3K-delta selective and broad spectrum PI3K inhibitors, an MEK inhibitor, a cyclin dependent kinase inhibitor, a b-RAF inhibitor, an mTOR inhibitor, a proteasome inhibitor (e.g., bortezomib, carfilzomib), an HDAC-inhibitor (e.g., panobinostat, vorinostat), a DNA methyl transferase inhibitor, dexamethasone, melphalan, or an immunomodulator (e.g., lenolidomide, pomalidomide).

In some embodiments, the compounds of the invention are administered in combination with ruxolitinib. In some embodiments, the compounds of the invention are administered in combination with the JAK1-selective inhibitor INCB039110.

In some embodiments, the compounds of the invention are administered in combination with a bortezomib, melphalan, and/or lenolidomide. In some embodiments, the compounds of the invention are administered in combination with melphalan. In some embodiments, the compounds of the invention are administered in combination with bortezomib. In some embodiments, the compounds of the invention are administered in combination with lenolidomide.

V. Formulation, Dosage Forms, and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

VI. Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating BET proteins in tissue samples, including human, and for identifying BET protein ligands by inhibition binding of a labeled compound. Accordingly, the present invention includes BET protein assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}$H (also written as T for tritium), $^{11}$C, 13C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro BET protein labeling and competition assays, compounds that incorporate $^{3}$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a BET protein by monitoring its concentration variation when contacting with the BET protein, through tracking of the labeling. For example, a test compound (labeled) can be evaluated for its ability to reduce binding of another compound which is known to bind to a BET protein (i.e., standard compound). Accordingly, the ability of a test compound to compete with the standard compound for binding to the BET protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

VII. Kits

The present invention also includes pharmaceutical kits useful, for example, in the treatment or prevention of BET protein-associated diseases or disorders, such as cancer, which include one or more containers containing a pharmaceutical composition comprising a therapeutically effective amount of a compound of Formula (I), or any of the embodiments thereof. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 m, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters XBridge $C_{18}$ 5 m, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

Intermediate 1

7-(3,5-Dimethylisoxazol-4-yl)-4-phenyl-4,5-dihydroimidazo[1,5,4-de][1,4]benzoxazin-2(1H)-one

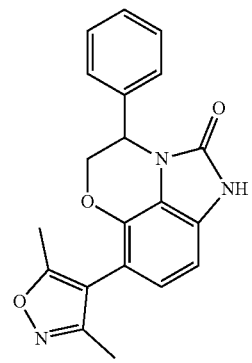 [SMILES: Cc1noc(C)c1-c1ccc2[nH]c(=O)n3c2c1OCC3c1ccccc1]

Step 1. 5-Nitro-3-phenyl-2H-1,4-benzoxazine

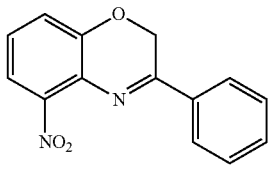 [SMILES: O=[N+]([O-])c1cccc2c1N=C(c1ccccc1)CO2]

The 2-bromoacetophenone (3.9 g, 19 mmol) [Aldrich, cat. #115835] was added portion wise to a stirred suspension of 2-amino-3-nitrophenol (2.5 g, 16 mmol) [Aldrich, cat. #297003] and $K_2CO_3$ (3.4 g, 24 mmol) in MeCN (100 mL) at room temperature. The reaction was monitored by LC/MS. After stirring for 3 h the reaction was complete and then EtOAc added and solution filtered to remove the solids and the organic layer was washed with water, 1 N HCl, brine, dried over $MgSO_4$, filtered and concentrated to give 5-nitro-3-phenyl-2H-1,4-benzoxazine as a dark oil (4.1 g, 100%). LCMS calc. for $C_{14}H_{11}N_2O_3$ $(M+H)^+$: m/z=255.3; found: 255.1.

Step 2. 3-Phenyl-3,4-dihydro-2H-1,4-benzoxazin-5-amine

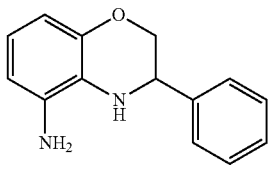 [SMILES: Nc1cccc2c1NC(c1ccccc1)CO2]

The 5-nitro-3-phenyl-2H-1,4-benzoxazine oil was taken up in MeOH (50 mL) in a Parr shaker bottle, deoxygenated with nitrogen, the catalyst 10% Pd on carbon (0.25 g) was added, the reaction vessel was charged to 55 psi with hydrogen and shaken. After 2 h the reaction was complete by LC/MS. The reaction was filtered to remove the catalyst and concentrated under reduced pressure to give 3-phenyl-3,4-dihydro-2H-1,4-benzoxazin-5-amine as a dark oil. (3.5 g, 97%). LCMS calc. for $Cl_4H_{15}N_2O$ $(M+H)^+$: m/z=227.1; found: 227.1. $^1H$ NMR (500 MHz, DMSO-$d_6$) δ 7.44 (d, J=7.4 Hz, 2H), 7.37 (dd, J=7.5 Hz, 2H), 7.31 (t, J=7.2 Hz, 1H), 6.35 (dd, J=7.9 Hz, 1H), 6.21 (dd, J=7.8, 1.0 Hz, 1H), 6.07 (d, J=7.9 Hz, 1H), 5.00 (s, 1H), 4.62 (s, 2H), 4.44 (dd, J=4.9, 2.6 Hz, 1H), 4.21-4.13 (m, 1H), 3.87 (dd, J=10.4, 7.7 Hz, 1H).

Step 3. 4-Phenyl-4,5-dihydroimidazo[1,5,4-de][1,4]benzoxazin-2(1H)-one

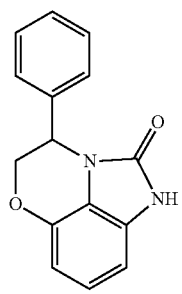 [SMILES: O=c1[nH]c2cccc3c2n1C(c1ccccc1)CO3]

The 3-phenyl-3,4-dihydro-2H-1,4-benzoxazin-5-amine (0.95 g, 4.2 mmol) was dissolved in THF (30 mL) and DIPEA (1.5 mL, 8.4 mmol) at room temperature (room temperature). The N,N-carbonyldiimidazole (0.82 g, 5.0 mmol) was added portion wise over 10 min. The reaction was heated to 70° C. for 1 h and allowed to cool to room temperature and stirred overnight. To the reaction mixture was added EtOAc, and then the mixture was washed with water, sodium bicarbonate water and brine, then dried over magnesium sulfate and concentrated to give crude product as a dark oil. The oil was triturated with ethyl ether to give a precipitate. The solids were triturated twice with ethyl ether and then the solids were collected and air dried to give 4-phenyl-4,5-dihydroimidazo[1,5,4-de][1,4]benzoxazin-2 (1H)-one as a brown solid (0.51 g, 48%). LCMS calc. for $C_{15}H_{13}N_2O_2$ $(M+H)^+$: m/z=253.1; found: 253.1. $^1H$ NMR (300 MHz, DMSO-$d_6$) δ 10.88 (s, 1H), 7.39-7.22 (m, 3H), 7.15-7.04 (m, 2H), 6.88 (t, J=8.0 Hz, 1H), 6.67 (d, J=7.8 Hz, 1H), 6.57 (d, J=8.2 Hz, 1H), 5.45 (s, 1H), 4.54 (dd, J=11.6, 2.2 Hz, 1H), 4.37 (dd, J=11.6, 3.0 Hz, 1H).

Step 4. 7-Bromo-4-phenyl-4,5-dihydroimidazo[1,5,4-de][1,4]benzoxazin-2(1H)-one

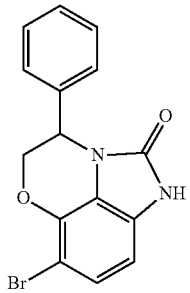 [SMILES: O=c1[nH]c2ccc(Br)c3c2n1C(c1ccccc1)CO3]

A mixture of 4-phenyl-4,5-dihydroimidazo[1,5,4-de][1,4]benzoxazin-2(1H)-one (400 mg, 2 mmol) and N-bromosuccinimide (310 mg, 1.7 mmol) in AcOH (10 mL) was stirred at room temperature for 2 h. The reaction mixture was allowed to cool and was concentrated to remove AcOH. The residue was taken up in EtOAc and was washed with water saturated $NaHCO_3$, brine, dried over magnesium sulfate, filtered and concentrated to give crude product. The product was purified by flash column chromatography on a Biotage system eluting with a hexane: EtOAc gradient (0-40%) to give 7-bromo-4-phenyl-4,5-dihydroimidazo[1,5,4-de][1,4]benzoxazin-2(1H)-one as an amber oil (0.30 g, 60%). LCMS calc. for $C_{15}H_{12}BrN_2O_2$ $(M+H)^+$: m/z=331.1, 333.1; found: 331.0, 333.0. $^1H$ NMR (300 MHz, $CD_3OD$) δ 7.42-7.23 (m, 3H), 7.23-7.09 (m, 3H), 6.70 (d, J=8.4 Hz, 1H), 5.46 (dd, J=2.6 Hz, 1H), 4.66 (dd, J=11.6, 2.4 Hz, 1H), 4.47 (dd, J=11.6, 3.1 Hz, 1H).

Step 5. 7-(3,5-Dimethylisoxazol-4-yl)-4-phenyl-4,5-dihydroimidazo[1,5,4-de][1,4]benzoxazin-2(1H)-one 7-Bromo-4-phenyl-4,5-dihydroimidazo[1,5,4-de][1,4]benzoxazin-2(1H)-one (200 mg, 0.6 mmol) and 3,5-dimethyl-4-(4,4,5,5-tetramethyl-1,3,2-dioxaborolan-2-yl)isoxazole (160 mg, 0.72 mmol) [Aldrich, cat. #643882] were dissolved in 1,4-dioxane (20 mL) and potassium carbonate (200 mg, 1 mmol) in water (8 mL). The reaction was deoxygenated with nitrogen and the catalyst [1,1'-bis(diphenylphosphino)ferrocene]dichloropalladium(II) complexed with DCM (1:1) (20 mg, 0.03 mmol) was added. The reaction mixture was deoxygenated with nitrogen and was heated at 100° C. After heating for 2 h the reaction was complete by LCMS. The reaction mixture was allowed to cool to room temperature, EtOAc was added and the mixture was washed with water, brine, then dried over magnesium sulfate and concentrated to give the crude product. The product was purified on preparative HPLC on a C-18 column eluting with a water:MeCN gradient buffered pH 2 with TFA to give 7-(3,5-dimethylisoxazol-4-yl)-4-phenyl-4,5-dihydroimidazo[1,5,4-de][1,4]benzoxazin-2(1H)-one as white solid (0.10 g, 50%). LCMS calc. for $C_{20}H_{18}N_3O_3$ (M+H)$^+$: m/z=348.1; found: 348.1. $^1$H NMR (500 MHz, DMSO-d$_6$) δ 10.96 (s, 1H), 7.38-7.24 (m, 3H), 7.16 (d, J=7.2 Hz, 2H), 6.84 (d, J=8.0 Hz, 1H), 6.76 (d, J=8.0 Hz, 1H), 5.47 (s, 1H), 4.57 (dd, J=11.6, 2.2 Hz, 1H), 4.40 (dd, J=11.6, 3.1 Hz, 1H), 2.25 (s, 3H), 2.08 (s, 3H).

Intermediate 2

7-(3,5-Dimethylisoxazol-4-yl)-4-pyridin-2-yl-4,5-dihydroimidazo[1,5,4-de][1,4]benzoxazin-2(1H)-one

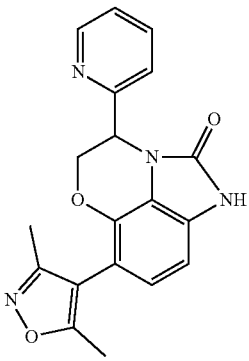

The title compound was prepared by methods analogous to Intermediate 1 but using 2-bromo-1-(pyridin-2-yl)ethanone HBr [Maybridge CC04005DA] in Step 1. The product was purified by preparative HPLC on a C-18 column eluting with a water:MeCN gradient buffered pH 2 with TFA to give the TFA salt of the title compound as a white amorphous solid (0.015 g, 30%). LCMS calc. for $C_{19}H_{17}N_4O_3$ (M+H)$^+$: m/z=349.1; found: 349.1. $^1$H NMR (300 MHz, DMSO-d$_6$) δ 11.01 (s, 1H), 8.52 (d, J=4.8 Hz, 1H), 7.79 (td, 1H), 7.32 (dd, J=7.5, 4.9 Hz, 1H), 7.12 (d, J=7.8 Hz, 1H), 6.83 (d, J=8.0 Hz, 1H), 6.76 (d, J=8.0 Hz, 1H), 5.52 (s, 1H), 4.76 (dd, 1H), 4.44 (dd, J=11.4, 3.1 Hz, 1H), 2.22 (s, 3H), 2.05 (s, 3H).

Intermediate 3

(4S)-7-(3,5-Dimethylisoxazol-4-yl)-4-pyridin-2-yl-4,5-dihydroimidazo[1,5,4-de][1,4]benzoxazin-2(1H)-one

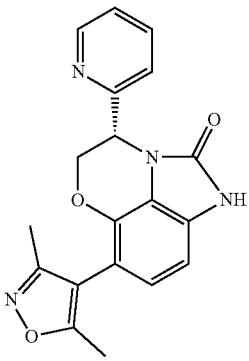 [SMILES: Cc1noc(C)c1-c1ccc2[nH]c(=O)n3c2c1OC[C@@H]3c1ccccn1]

This enantiomer was isolated from racemic 7-(3,5-dimethylisoxazol-4-yl)-4-pyridin-2-yl-4,5-dihydroimidazo[1,5,4-de][1,4]benzoxazin-2(1H)-one from Intermediate 2 by chiral column HPLC using a Phenomenex Lux Cellulose-C4 column, 5 micron, 21.2×250 mm, eluting with 60% ethanol in hexanes with a flow rate of 18 mL/min., loading approx. 36 mg per injection with UV (220 nm) detection. LCMS calc. for $C_{19}H_{17}N_4O_3$ (M+H)$^+$: m/z=349.1; found: 349.1. $^1$H NMR (300 MHz, DMSO-d$_6$) δ 11.01 (s, 1H), 8.52 (d, J=4.8 Hz, 1H), 7.79 (td, 1H), 7.32 (dd, J=7.5, 4.9 Hz, 1H), 7.12 (d, J=7.8 Hz, 1H), 6.83 (d, J=8.0 Hz, 1H), 6.76 (d, J=8.0 Hz, 1H), 5.52 (s, 1H), 4.76 (dd, 1H), 4.44 (dd, J=11.4, 3.1 Hz, 1H), 2.22 (s, 3H), 2.05 (s, 3H).

Intermediate 4

(4S)-2-Chloro-7-(3,5-dimethylisoxazol-4-yl)-4-pyridin-2-yl-4,5-dihydroimidazo[1,5,4-de][1,4]benzoxazine

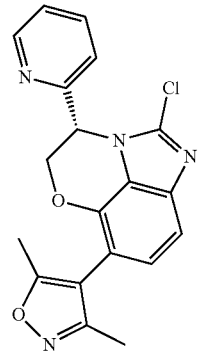 [SMILES: Cc1noc(C)c1-c1ccc2nc(Cl)n3c2c1OC[C@@H]3c1ccccn1]

To a solution of (4S)-7-(3,5-dimethylisoxazol-4-yl)-4-pyridin-2-yl-4,5-dihydroimidazo[1,5,4-de][1,4]benzoxazin-2(1H)-one (9.0 g, 20 mmol) and 4-methylmorpholine (5.7 mL, 52 mmol) in 1,4-dioxane (300 mL) at room temperature, triphosgene (2.8 g, 9.6 mmol) in 1,4-dioxane (50 mL) was added. After stirring at room temperature for 3 h, the reaction mixture was added dropwise into a mixture of saturated sodium bicarbonate (200 mL) and ice (100 g) over 15 minutes. After stirring at room temperature for 20 minutes, the mixture was extracted with dichloromethane (3×200 mL). The combined organic extracts were dried over sodium sulfate, filtered, and concentrated under vacuum. Purification on silica gel using 70%-100% ethyl acetate in hexanes afforded the desired product, (2.0 g, 20%). LCMS calc. for $C_{19}H_{16}O_2N_4Cl$ (M+H)$^+$: m/z=367.1; found: 367.1.

Example 1

(4S)-7-(3,5-Dimethylisoxazol-4-yl)-2-(4-isobutyrylpiperazin-1-yl)-4-pyridin-2-yl-4,5-dihydroimidazo[1,5,4-de][1,4]benzoxazine

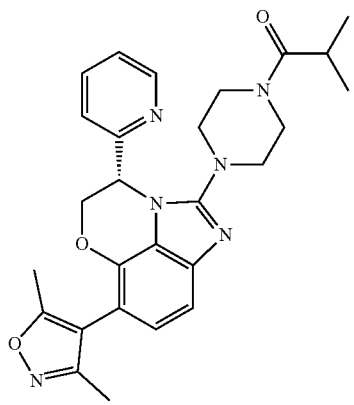 [SMILES: Cc1noc(C)c1-c1ccc2nc(N3CCN(C(=O)C(C)C)CC3)n3c2c1OC[C@@H]3c1ccccn1]

Step 1. tert-Butyl 4-[(4S)-7-(3,5-imethylisoxazol-4-yl)-4-pyridin-2-yl-4,5-dihydroimidazo[1,5,4-de][1,4]benzoxazin-2-yl]piperazine-1-carboxylate

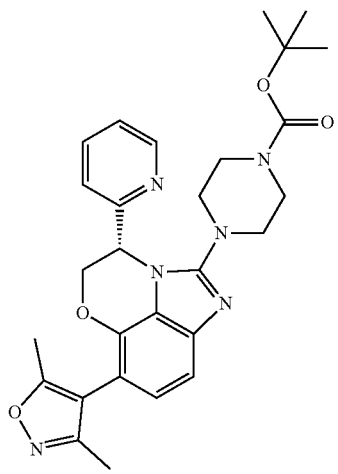 [SMILES: Cc1noc(C)c1-c1ccc2nc(N3CCN(C(=O)OC(C)(C)C)CC3)n3c2c1OC[C@@H]3c1ccccn1]

(4S)-2-Chloro-7-(3,5-dimethylisoxazol-4-yl)-4-pyridin-2-yl-4,5-dihydroimidazo[1,5,4-de][1,4]benzoxazine (Intermediate 4, 5.8 g, 16 mmol), tert-butyl piperazine-1-carboxylate (58.9 g, 320 mmol) and triethylamine (11 mL, 79 mmol) were stirred in N-methylpyrrolidinone (200 mL) overnight at 80° C. The mixture was cooled to room temperature, poured over ethyl acetate, washed with brine, dried over sodium sulfate, filtered and evaporated. Purification by preparative LCMS (pH 10) gave the desired compound (3.1 g, 38%). LCMS calc. for $C_{28}H_{33}N_6O_4$ (M+H)$^+$: m/z=517.3; found: 517.4.

Step 2. (4S)-7-(3,5-Dimethylisoxazol-4-yl)-2-piperazin-1-yl-4-pyridin-2-yl-4,5-dihydroimidazo[1,5,4-de][1,4]benzoxazine trihydrochloride

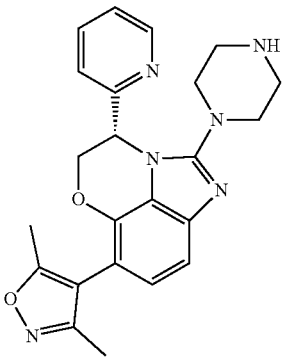 [SMILES: Cc1noc(C)c1-c1ccc2nc(N3CCNCC3)n3c2c1OC[C@@H]3c1ccccn1]

tert-Butyl 4-[(4S)-7-(3,5-dimethylisoxazol-4-yl)-4-pyridin-2-yl-4,5-dihydroimidazo[1,5,4-de][1,4]benzoxazin-2-yl]piperazine-1-carboxylate (45 mg, 0.087 mmol) was stirred in 4 N HCl in dioxane (3 mL) and methanol (2 mL) for 30 min and evaporated to give the title compound (45 mg, 92%). LCMS calc. for $C_{23}H_{25}N_6O_2$ (M+H)$^+$: m/z=417.2; found: 417.3.

Step 3. (4S)-7-(3,5-Dimethylisoxazol-4-yl)-2-(4-isobutyrylpiperazin-1-yl)-4-pyridin-2-yl-4,5-dihydroimidazo[1,5,4-de][1,4]benzoxazine To a solution of (4S)-7-(3,5-dimethylisoxazol-4-yl)-2-piperazin-1-yl-4-pyridin-2-yl-4,5-dihydroimidazo[1,5,4-de][1,4]benzoxazine trihydrochloride (600.0 mg, 1.1 mmol) in methylene chloride (29 mL), was added triethylamine (790 µL, 5.7 mmol). The mixture was cooled to 0° C., isobutyryl chloride (240 µL, 2.3 mmol) was added and the mixture was stirred for 5 min. The mixture was diluted with methanol and purified on preparative LCMS using pH 10 buffer to give the desired product. LCMS calc. for $C_{27}H_{31}N_6O_3$ (M+H)$^+$: m/z=487.2; found: 487.1. $^1$H NMR (500 MHz, DMSO-d6) δ 8.60-8.55 (m, 1H), 7.79 (td, J=7.8, 1.7 Hz, 1H), 7.36 (dd, J=7.5, 4.9 Hz, 1H), 7.11 (d, J=8.1 Hz, 1H), 6.90 (dd, J=8.1, 3.5 Hz, 1H), 6.04 (t, J=2.8 Hz, 1H), 4.66 (ddd, J=66.7, 11.5, 3.0 Hz, 2H), 3.48 (d, J=12.5 Hz, 4H), 3.32 (s, 4H), 2.85 (p, J=6.8 Hz, 1H), 2.24 (s, 3H), 2.07 (s, 3H), 0.98 (d, J=6.7 Hz, 6H).

Example 2

(4S)-2-[(2R,6S)-4-Acetyl-2,6-dimethylpiperazin-1-yl]-7-(3,5-dimethylisoxazol-4-yl)-4-pyridin-2-yl-4,5-dihydroimidazo[1,5,4-de][1,4]benzoxazine

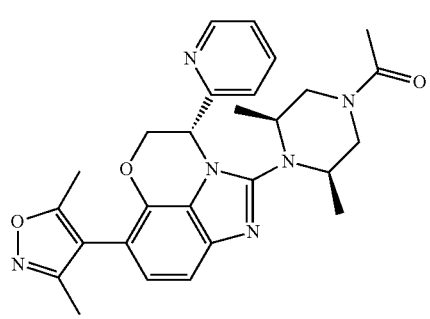 [SMILES: CC(=O)N1C[C@@H](C)N(c2nc3ccc(-c4c(C)noc4C)c4c3n2[C@@H](c2ccccn2)CO4)[C@@H](C)C1]

The title compound was prepared by methods analogous to Example 1 (steps 1-3), but substituting tert-butyl (3R, 5S)-3,5-dimethylpiperazine-1-carboxylate in step 1 and acetyl chloride in step 3. The mixture was evaporated and purified by preparative LCMS using pH 10 buffer to give two atropisomers. Only the second eluting isomer was obtained. LCMS calc. for $C_{27}H_{31}N_6O_3$ (M+H)$^+$: m/z=487.2; found: 487.1.

Examples 3-29

Compounds of Examples 3-29 are provided in Table 1 below together with their synthetic procedure.

TABLE 1

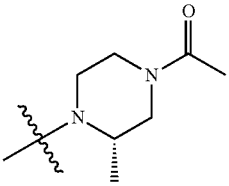 [SMILES: *N1CCN(C(C)=O)C[C@@H]1C]

| Ex. No. | Name | Cy$^1$ | Procedure (Ex. No.) |
|---|---|---|---|
| 3 | (4S)-2-[(2S)-4-acetyl-2-methylpiperazin-1-yl]-7-(3,5-dimethylisoxazol-4-yl)-4-pyridin-2-yl-4,5-dihydroimidazo[1,5,4-de][1,4]benzoxazine | 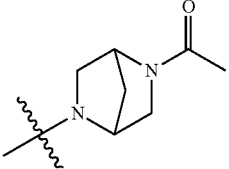 [SMILES: *N1CC2CC1CN2C(C)=O] | 1 |
| 4 | (4S)-2-(5-acetyl-2,5-diazabicyclo[2.2.1]hept-2-yl)-7-(3,5-dimethylisoxazol-4-yl)-4-pyridin-2-yl-4,5-dihydroimidazo[1,5,4-de][1,4]benzoxazine | 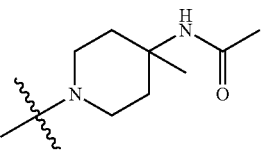 [SMILES: *N1CCC(C)(NC(C)=O)CC1] | 1 |
| 5 | N-{1-[(4S)-7-(3,5-dimethylisoxazol-4-yl)-4-pyridin-2-yl-4,5-dihydroimidazo[1,5,4-de][1,4]benzoxazin-2-yl]-4-methylpiperidin-4-yl}acetamide | 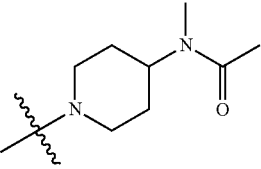 [SMILES: *N1CCC(N(C)C(C)=O)CC1] | 1 |
| 6 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N-methylacetamide | 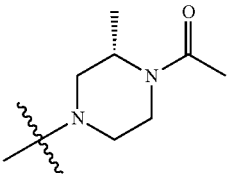 [SMILES: *N1CCN(C(C)=O)[C@@H](C)C1] | 1 |
| 7 | (4S)-2-[(3S)-4-acetyl-3-methylpiperazin-1-yl]-7-(3,5-dimethylisoxazol-4-yl)-4-pyridin-2-yl-4,5-dihydroimidazo[1,5,4-de][1,4]benzoxazine |  | 1 |

TABLE 1-continued

| Ex. No. | Name | Cy¹ | Procedure (Ex. No.) |
|---|---|---|---|
| 8 | (4S)-7-(3,5-dimethylisoxazol-4-yl)-2-[(3S)-3-methyl-4-propionylpiperazin-1-yl]-4-pyridin-2-yl-4,5-dihydroimidazo[1,5,4-de][1,4]benzoxazine | | 1 |
| 9 | (4S)-7-(3,5-dimethylisoxazol-4-yl)-2-[(3S)-4-isobutyryl-3-methylpiperazin-1-yl]-4-pyridin-2-yl-4,5-dihydroimidazo[1,5,4-de][1,4]benzoxazine | | 1 |
| 10 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}butanamide | | 1 |
| 11 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-2,2-dimethylpropanamide | | 1 |
| 12 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}cyclobutanecarboxamide | | 1 |
| 13 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}cyclobutanecarboxamide | | 1 |
| 14 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}ethanesulfonamide | | 1 |

TABLE 1-continued

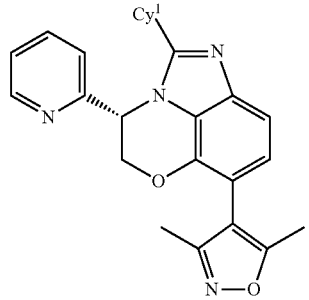

| Ex. No. | Name | Cy¹ | Procedure (Ex. No.) |
|---|---|---|---|
| 15 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N-methylpropanamide | 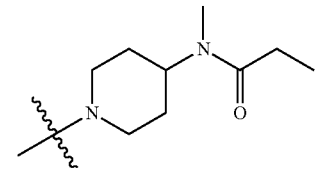 | 1 |
| 16 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N-methylbutanamide | 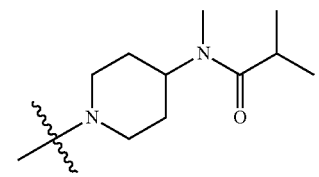 | 1 |
| 17 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N,2-dimethylpropanamide | 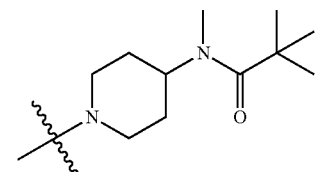 [SMILES: *N1CCC(NC(=O)C(C)(C)C)CC1] | 1 |
| 18 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N,2,2-trimethylpropanamide | 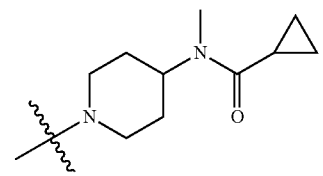 [SMILES: *N1CCC(N(C)C(=O)C2CC2)CC1] | 1 |
| 19 | N-{1-[(4S)-7-(3,5-dimelhylisoxazol-4-yl)-4-pyridin-2-yl-4,5-dihydroimidazo[1,5,4-de][1,4]benzoxazin-2-yl]piperidin-4-yl}-N-methylcyclopropanecarboxamide | 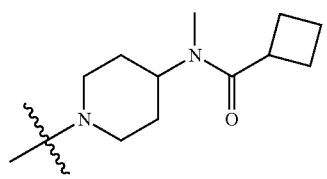 [SMILES: *N1CCC(N(C)C(=O)C2CCC2)CC1] | 1 |
| 20 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N-methylcyclobutanecarboxamide |  | 1 |

TABLE 1-continued

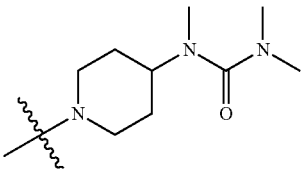 [SMILES: *N1CCC(N(C)C(=O)N(C)C)CC1]

| Ex. No. | Name | Cy¹ | Procedure (Ex. No.) |
|---|---|---|---|
| 21 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N,N',N'-trimethylurea | 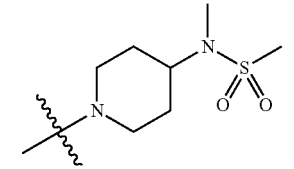 [SMILES: *N1CCC(N(C)S(C)(=O)=O)CC1] | 1 |
| 22 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N-methylmethanesulfonamide | 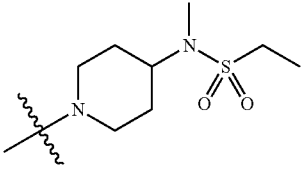 [SMILES: *N1CCC(N(C)S(=O)(=O)CC)CC1] | 1 |
| 23 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N-methylethanesulfonamide | 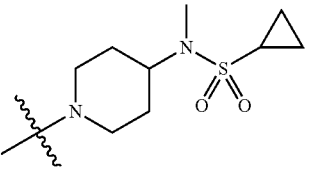 [SMILES: *N1CCC(N(C)S(=O)(=O)C2CC2)CC1] | 1 |
| 24 | N-{1-[(4S)-7-(3,5-dimethylisoxazol-4-yl)-4-pyridin-2-yl-4,5-dihydroimidazo[1,5,4-de][1,4]benzoxazin-2-yl]piperidin-4-yl}-N-methylcyclopropanesulfonamide | 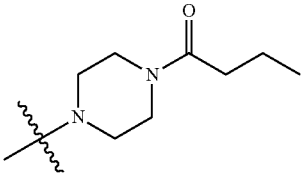 [SMILES: *N1CCN(C(=O)CCC)CC1] | 1 |
| 25 | (4S)-2-(4-butyrylpiperazin-1-yl)-7-(3,5-dimethylisoxazol-4-yl)-4-pyridin-2-yl-4,5-dihydroimidazo[1,5,4-de][1,4]benzoxazine | 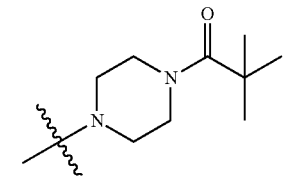 [SMILES: *N1CCN(C(=O)C(C)(C)C)CC1] | 1 |
| 26 | (4S)-7-(3,5-dimethylisoxazol-4-yl)-2-[4-(2,2-dimethylpropanoyl)piperazin-1-yl]-4-pyridin-2-yl-4,5-dihydroimidazo[1,5,4-de][1,4]benzoxazine | | 1 |

TABLE 1-continued

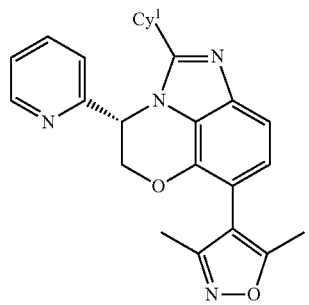

| Ex. No. | Name | Cy¹ | Procedure (Ex. No.) |
|---|---|---|---|
| 27 | (4S)-2-[4-(cyclopropylcarbonyl)piperazin-1-yl]-7-(3,5-dimethylisoxazol-4-yl)-4-pyridin-2-yl-4,5-dihydroimidazo[1,5,4-de][1,4]benzoxazine | | 1 |
| 28 | (4S)-2-[4-(cyclobutylcarbonyl)piperazin-1-yl]-7-(3,5-dimethylisoxazol-4-yl)-4-pyridin-2-yl-4,5-dihydroimidazo[1,5,4-de][1,4]benzoxazine | | 1 |
| 29 | (4S)-7-(3,5-dimethylisoxazol-4-yl)-2-[4-(methoxyacetyl)piperazin-1-yl]-4-pyridin-2-yl-4,5-dihydroimidazo[1,5,4-de][1,4]benzoxazine | | 1 |

Analytical Data $^1$H NMR data (Varian Inova 500 spectrometer, a Mercury 400 spectrometer, or a Varian (or Mercury) 300 spectrometer) and LCMS mass spectral data (MS) for the compounds of Examples 3 to 29 are provided below in Table 2.

TABLE 2

| Example No. | MS [M + H]⁺ | ¹H NMR Spectrum |
|---|---|---|
| 3 | 473.3 | ¹H NMR (400 MHz, CD₃OD) δ 8.58 (d, J = 4.2 Hz, 1H), 7.85-7.69 (m, 1H), 7.43-7.32 (m, 1H), 7.19 (d, J = 8.2 Hz, 1H), 7.00 (d, J = 8.2 Hz, 1H), 6.90 (dd, J = 7.9, 3.6 Hz, 1H), 5.84 (s, 1H), 4.67 (t, J = 4.3 Hz, 2H), 3.90 (s, 1H), 3.63 (s, 1H), 3.33 (s, 3H), 3.09 (s, 1H), 2.92 (d, J = 31.2 Hz, 1H), 2.28 (s, 3H), 2.13 (s, 3H), 2.09 (d, 3H), 1.05 (dd, J = 16.9, 6.5 Hz, 3H). |
| 4 | 471.3 | |
| 5 | 487.3 | |
| 6 | 487.3 | |
| 7 | 473.3 | |
| 8 | 487.3 | ¹H NMR (400 MHz, CD₃OD) δ 8.58 (d, J = 4.2 Hz, 1H), 7.72 (td, J = 7.8, 1.7 Hz, 1H), 7.33 (dd, J = 7.0, 5.1 Hz, 1H), 7.18 (d, J = 8.2 Hz, 1H), 6.98 (d, J = 8.2 Hz, 1H), 6.60 (d, J = 8.0 Hz, 1H), 5.94 (s, 1H), 4.88 (s, 1H), 4.70 (s, 1H), 4.60 (dd, J = 11.6, 2.8 Hz, 1H), 4.16 (s, 1H), 3.75 (m, 3H), 3.21 (s, 2H), 2.33 (s, 2H), 2.24 (s, 3H), 2.09 (s, 3H), 1.08 (s, 3H), 0.94 (m, 3H). |

TABLE 2-continued

| Example No. | MS [M + H]+ | 1H NMR Spectrum |
|---|---|---|
| 9 | 501.3 | |
| 10 | 501.3 | 1H NMR (400 MHz, CD3OD) δ 8.57-8.39 (m, 1H), 7.66 (td, J = 7.8, 1.8 Hz, 1H), 7.27 (dd, J = 6.6, 4.9 Hz, 1H), 7.06 (d, J = 8.2 Hz, 1H), 6.86 (d, J = 8.2 Hz, 1H), 6.70 (d, J = 7.9 Hz, 1H), 5.76 (t, J = 3.1 Hz, 1H), 4.66-4.37 (m, 2H), 3.81-3.56 (m, 3H), 3.07-2.85 (m, 2H), 2.17 (s, 3H), 2.08-1.90 (m, 5H), 1.79-1.61 (m, 2H), 1.50 (q, J = 7.4 Hz, 2H), 1.41-1.27 (m, 1H), 1.11 (d, J = 11.7 Hz, 1H), 0.82 (t, J = 7.4 Hz, 3H). |
| 11 | 515.3 | 1H NMR (400 MHz, CD3OD) δ 8.65-8.49 (m, 1H), 7.75 (td, J = 7.8, 1.8 Hz, 1H), 7.36 (dd, J = 7.2, 5.4 Hz, 1H), 7.15 (d, J = 8.2 Hz, 1H), 6.96 (d, J = 8.2 Hz, 1H), 6.77 (d, J = 8.0 Hz, 1H), 6.00-5.76 (m, 1H), 4.80-4.46 (m, 2H), 3.82 (m, 3H), 3.05 (m, 2H), 2.26 (s, 3H), 2.11 (s, 3H), 1.76 (m, 2H), 1.63-1.44 (m, 1H), 1.42-1.23 (m, 1H), 1.14 (s, 9H). |
| 12 | 499.3 | 1H NMR (400 MHz, CD3OD) δ 8.60-8.41 (m, 1H), 7.67 (td, J = 7.8, 1.8 Hz, 1H), 7.44-7.18 (m, 1H), 7.06 (d, J = 8.2 Hz, 1H), 6.86 (d, J = 8.2 Hz, 1H), 6.79-6.61 (m, 1H), 5.87-5.68 (m, 1H), 4.67-4.39 (m, 2H), 3.82-3.54 (m, 3H), 3.08-2.84 (m, 2H), 2.17 (s, 3H), 2.02 (s, 3H), 1.69 (s, 2H), 1.51-1.24 (m, 2H), 1.14 (s, 1H), 0.71 (dd, J = 4.6, 2.8 Hz, 2H), 0.62 (dt, J = 8.0, 3.0 Hz, 2H). |
| 13 | 513.3 | 1H NMR (400 MHz, CD3OD) δ 8.49 (d, J = 4.8 Hz, 1H), 7.86-7.47 (m, 1H), 7.27 (dd, J = 7.5, 5.0 Hz, 1H), 7.05 (d, J = 8.2 Hz, 1H), 6.87 (d, J = 8.2 Hz, 1H), 6.70 (d, J = 7.9 Hz, 1H), 5.77 (d, J = 3.1 Hz, 1H), 4.70-4.33 (m, 2H), 3.92-3.50 (m, 3H), 3.12-2.77 (m, 3H), 2.17 (s, 3H), 2.15-2.05 (m, 1H), 2.02 (s, 3H), 1.98 (d, J = 9.3 Hz, 1H), 1.86 (d, J = 10.2 Hz, 1H), 1.69 (d, J = 14.2 Hz, 3H), 1.35 (s, 2H), 1.12 (s, 2H). |
| 14 | 523.3 | 1H NMR (400 MHz, CD3OD) δ 8.59 (d, J = 4.9 Hz, 1H), 7.76 (td, J = 7.8, 1.8 Hz, 1H), 7.37 (dd, J = 7.1, 5.4 Hz, 1H), 7.15 (d, J = 8.2 Hz, 1H), 6.96 (d, J = 8.2 Hz, 1H), 6.80 (d, J = 7.9 Hz, 1H), 5.85 (t, J = 3.2 Hz, 1H), 4.76-4.46 (m, 2H), 3.93-3.64 (m, 2H), 3.30 (m, 2H), 3.14-2.90 (m, 4H), 2.26 (s, 3H), 2.11 (s, 3H), 1.97-1.76 (m, 2H), 1.62-1.39 (m, 1H), 1.29 (t, J = 7.4 Hz, 4H). |
| 15 | 501.3 | 1H NMR (400 MHz, CD3OD) δ 8.60 (s, 1H), 7.90-7.68 (m, 1H), 7.48-7.30 (m, 1H), 7.16 (dd, J = 8.2, 3.7 Hz, 1H), 6.97 (dd, J = 8.2, 3.4 Hz, 1H), 6.94-6.77 (m, 1H), 5.96-5.75 (m, 1H), 4.73-4.35 (m, 3H), 3.87 (s, 2H), 3.13-2.95 (m, 2H), 2.72 (d, J = 46.0 Hz, 3H), 2.51-2.31 (m, 2H), 2.27 (d, J = 2.0 Hz, 3H), 2.12 (d, J = 2.2 Hz, 3H), 1.88-1.24 (m, 4H), 1.16-1.02 (m, 3H). |
| 16 | 515.3 | 1H NMR (400 MHz, CD3OD) δ 8.68-8.53 (m, 1H), 7.87-7.68 (m, 1H), 7.49-7.29 (m, 1H), 7.16 (dd, J = 8.2, 4.2 Hz, 1H), 6.97 (dd, J = 8.2, 3.9 Hz, 2H), 5.87 (t, J = 3.3 Hz, 1H), 4.75-4.40 (m, 3H), 3.89 (s, 2H), 3.17-2.92 (m, 2H), 2.72 (d, J = 51.9 Hz, 3H), 2.36 (dt, J = 29.9, 7.6 Hz, 2H), 2.27 (d, J = 2.3 Hz, 3H), 2.12 (d, J = 2.5 Hz, 3H), 1.86-1.23 (m, 6H), 0.95 (td, J = 7.4, 2.0 Hz, 3H). |
| 17 | 515.3 | 1H NMR (400 MHz, CD3OD) δ 8.60 (s, 1H), 7.88-7.68 (m, 1H), 7.48-7.30 (m, 1H), 7.16 (dd, J = 8.2, 4.2 Hz, 1H), 7.02-6.79 (m, 2H), 5.87 (s, 1H), 4.76-4.35 (m, 3H), 3.93 (s, 2H), 2.74 (d, J = 69.3 Hz, 6H), 2.27 (d, J = 2.4 Hz, 3H), 2.12 (d, J = 2.6 Hz, 3H), 1.57 (s, 4H), 1.07 (t, J = 6.3 Hz, 6H). |
| 18 | 529.3 | 1H NMR (400 MHz, CD3OD) δ 8.60 (d, J = 4.9 Hz, 1H), 7.80 (td, J = 7.8, 1.8 Hz, 1H), 7.39 (dd, J = 6.6, 4.9 Hz, 1H), 7.16 (d, J = 8.2 Hz, 1H), 6.94 (dd, J = 26.8, 8.0 Hz, 2H), 5.88 (t, J = 3.3 Hz, 1H), 4.69-4.56 (m, 2H), 4.17 (s, 1H), 3.99-3.76 (m, 1H), 3.30 (p, J = 1.6 Hz, 3H), 3.05 (t, J = 12.7 Hz, 1H), 2.76 (s, 1H), 2.27 (s, 3H), 2.12 (s, 3H), 1.94-1.32 (m, 4H), 1.26 (s, 9H). |
| 19 | 513.3 | 1H NMR (400 MHz, CD3OD) δ 8.61 (s, 1H), 7.79 (s, 1H), 7.39 (s, 1H), 7.23-7.08 (m, 1H), 7.04-6.80 (m, 2H), 5.88 (s, 1H), 4.64 (s, 3H), 3.84 (s, 2H), 3.21-2.57 (m, 5H), 2.27 (s, 3H), 2.12 (s, 3H), 1.45 (s, 4H), 0.97-0.68 (m, 4H). |
| 20 | 527.3 | 1H NMR (400 MHz, CD3OD) δ 8.59 (s, 1H), 7.86-7.70 (m, 1H), 7.48-7.32 (m, 1H), 7.16 (dd, J = 8.2, 3.7 Hz, 1H), 7.06-6.79 (m, 2H), 5.99-5.79 (m, 1H), 4.75-4.34 (m, 3H), 3.36 (s, 4H), 3.17-2.93 (m, 2H), 2.66 (d, J = 20.0 Hz, 3H), 2.19 (dd, J = 59.8, 2.5 Hz, 9H), 2.07-1.30 (m, 6H). |
| 21 | 516.3 | 1H NMR (400 MHz, CD3OD) δ 8.58 (d, J = 4.9 Hz, 1H), 7.81 (td, J = 7.8, 1.8 Hz, 1H), 7.42-7.36 (m, 1H), 7.15 (d, J = 8.2 Hz, 1H), 7.03-6.94 (m, 2H), 5.93 (s, 1H), 4.73-4.58 (m, 2H), 3.90 (s, 2H), 3.68 (s, 1H), 3.07 (s, 2H), 2.78 (s, 6H), 2.65 (d, J = 35.5 Hz, 3H), 2.26 (s, 3H), 2.11 (s, 3H), 1.86-1.24 (m, 4H). |

TABLE 2-continued

| Example No. | MS [M + H]+ | ¹H NMR Spectrum |
|---|---|---|
| 22 | 523.3 | ¹H NMR (400 MHz, CD₃OD) δ 8.60 (d, J = 4.1 Hz, 1H), 7.79 (td, J = 7.8, 1.7 Hz, 1H), 7.38 (dd, J = 6.6, 4.9 Hz, 1H), 7.16 (d, J = 8.2 Hz, 1H), 6.96 (d, J = 8.2 Hz, 1H), 6.88 (d, J = 7.9 Hz, 1H), 5.86 (t, J = 3.4 Hz, 1H), 4.68-4.55 (m, 2H), 3.83 (d, J = 11.0 Hz, 3H), 3.08-2.96 (m, 2H), 2.87 (s, 3H), 2.66 (s, 3H), 2.27 (s, 3H), 2.12 (s, 3H), 1.85-1.50 (m, 3H), 1.40 (dd, J = 12.5, 4.3 Hz, 1H). |
| 23 | 537.3 | ¹H NMR (400 MHz, CD₃OD) δ 8.60 (d, J = 4.0 Hz, 1H), 7.79 (td, J = 7.8, 1.8 Hz, 1H), 7.38 (dd, J = 6.6, 4.9 Hz, 1H), 7.15 (d, J = 8.2 Hz, 1H), 6.96 (d, J = 8.2 Hz, 1H), 6.88 (d, J = 7.9 Hz, 1H), 5.86 (t, J = 3.4 Hz, 1H), 4.68-4.55 (m, 2H), 3.77 (d, J = 4.2 Hz, 3H), 3.03 (q, J = 7.4 Hz, 4H), 2.67 (s, 3H), 2.27 (s, 3H), 2.12 (s, 3H), 1.81-1.50 (m, 3H), 1.42 (dd, J = 12.3, 4.1 Hz, 1H), 1.27 (t, J = 7.4 Hz, 3H). |
| 24 | 549.2 | ¹H NMR (400 MHz, CD₃OD) δ 8.60 (d, J = 4.1 Hz, 1H), 7.80 (td, J = 7.8, 1.8 Hz, 1H), 7.39 (dd, J = 7.1, 5.4 Hz, 1H), 7.16 (d, J = 8.2 Hz, 1H), 6.94 (dd, J = 26.4, 8.0 Hz, 2H), 5.88 (t, J = 3.4 Hz, 1H), 4.70-4.56 (m, 2H), 3.85 (d, J = 11.8 Hz, 3H), 3.05 (t, J = 11.5 Hz, 2H), 2.69 (s, 3H), 2.54-2.45 (m, 1H), 2.27 (s, 3H), 2.12 (s, 3H), 1.69 (d, J = 50.3 Hz, 3H), 1.48-1.40 (m, 1H), 1.07-0.95 (m, 4H). |
| 25 | 487.1 | ¹H NMR (400 MHz, CD₃OD) δ 8.59 (d, J = 4.1 Hz, 1H), 7.77 (td, J = 7.8, 1.8 Hz, 1H), 7.37 (dd, J = 6.6, 4.9 Hz, 1H), 7.18 (d, J = 8.2 Hz, 1H), 6.98 (d, J = 8.2 Hz, 1H), 6.87 (d, J = 7.9 Hz, 1H), 5.90 (t, J = 3.3 Hz, 1H), 4.77-4.50 (m, 2H), 3.49 (m, 3H), 3.38 (m, 5H), 2.42-2.29 (m, 2H), 2.27 (s, 3H), 2.12 (s, 3H), 1.60 (q, J = 7.5 Hz, 2H), 0.95 (t, J = 7.4 Hz, 3H). |
| 26 | 501.3 | ¹H NMR (400 MHz, CD₃OD) δ 8.59 (d, J = 4.1 Hz, 1H), 7.77 (td, J = 7.8, 1.7 Hz, 1H), 7.37 (dd, J = 7.1, 5.4 Hz, 1H), 7.18 (d, J = 8.2 Hz, 1H), 6.98 (d, J = 8.2 Hz, 1H), 6.87 (d, J = 8.0 Hz, 1H), 5.90 (t, J = 3.3 Hz, 1H), 4.82-4.45 (m, 2H), 3.65-3.51 (m, 4H), 3.44-3.27 (m, 4H), 2.27 (s, 3H), 2.12 (s, 3H), 1.25 (s, 9H). |
| 27 | 485.3 | ¹H NMR (400 MHz, CD₃OD) δ 8.59 (d, J = 4.0 Hz, 1H), 7.78 (td, J = 7.8, 1.7 Hz, 1H), 7.38 (dd, J = 6.6, 4.9 Hz, 1H), 7.18 (d, J = 8.2 Hz, 1H), 6.98 (d, J = 8.2 Hz, 1H), 6.88 (d, J = 7.9 Hz, 1H), 5.91 (t, J = 3.3 Hz, 1H), 4.79-4.47 (m, 2H), 3.71 (m, 4H), 3.30 (m, 4H), 2.27 (s, 3H), 2.12 (s, 3H), 1.98-1.89 (m, 1H), 0.90-0.76 (m, 4H). |
| 28 | 499.3 | ¹H NMR (400 MHz, CD₃OD) δ 8.59 (d, J = 4.1 Hz, 1H), 7.77 (td, J = 7.8, 1.8 Hz, 1H), 7.37 (dd, J = 6.7, 4.9 Hz, 1H), 7.17 (d, J = 8.2 Hz, 1H), 6.98 (d, J = 8.2 Hz, 1H), 6.87 (d, J = 8.0 Hz, 1H), 5.89 (t, J = 3.3 Hz, 1H), 4.78-4.47 (m, 2H), 3.55 (d, J = 3.5 Hz, 1H), 3.48-3.15 (m, 8H), 2.38-2.07 (m, 10H), 2.07-1.90 (m, 1H), 1.83 (s, 1H). |
| 29 | 489.2 | ¹H NMR (400 MHz, CD₃OD) δ 8.59 (d, J = 4.1 Hz, 1H), 7.77 (td, J = 7.8, 1.8 Hz, 1H), 7.37 (dd, J = 6.6, 4.9 Hz, 1H), 7.18 (d, J = 8.2 Hz, 1H), 6.98 (d, J = 8.2 Hz, 1H), 6.88 (d, J = 8.0 Hz, 1H), 6.02-5.77 (m, 1H), 4.78-4.48 (m, 2H), 4.14 (s, 2H), 3.57 (s, 1H), 3.49-3.24 (m, 10H), 2.27 (s, 3H), 2.12 (s, 3H). |

Example A1

BRD4 AlphaScreen™ Assay

BRD4-BD1 and BRD4-BD2 assays were conducted in white 384-well polystyrene plate in a final volume of 20 μL for BD1 and 40 μL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature for 75 min. in the assay buffer (50 mM HEPES, pH 7.4, 100 mM NaCl, 0.05% CHAPS, 0.01% BSA), containing 50 nM Biotin-labeled tetra-acetylated histone H4 peptide (H4Ac4), 3.8 nM (BRD4-BD1, BPS Bioscience #31040) or 20 nM (BRD4-BD2, BPS Bioscience #31041). The reaction followed by the addition of 20 μL of assay buffer supplemented with Streptavidin donor beads (PerkinElmer 6760002) and GSH Acceptor beads (PerkinElmer-AL109C) at 4 μg/mL under reduced light. After plate sealing, the plate was incubated in the dark at room temperature for 75 min. before reading on a PHERAstar FS plate reader (BMG Labtech). $IC_{50}$ determination was performed by fitting the curve of percent control activity versus the log of the inhibitor concentration using the GraphPad Prism 5.0 software. Compounds of the invention are considered to be active BET inhibitors if their $IC_{50}$ in the BRD4-BD1 Assay is 6 μM or less. Compounds of the invention are considered to be active BET inhibitors if their $IC_{50}$ in the BRD4-BD2 Assay is 4 μM or less. Examples 1-29 of the invention have been tested in the BRD4-BD1 Assay and the BRD4-BD1 Assay and were found to be active BET inhibitors.

$IC_{50}$ data for the compounds of Examples 1 to 29 as determined by Assay A1 is presented in Table 3.

TABLE 3

| Example No. | BRD4 BD-1 enzyme IC$_{50}$ (nM)* | BRD4 BD-2 enzyme IC$_{50}$ (nM)* |
|---|---|---|
| 1 | + | + |
| 2 | + | + |
| 3 | ++ | + |
| 4 | + | + |
| 5 | ++ | + |
| 6 | + | + |
| 7 | + | + |
| 8 | + | + |
| 9 | + | + |
| 10 | + | + |
| 11 | + | + |
| 12 | + | + |
| 13 | + | + |
| 14 | + | + |
| 15 | + | + |
| 16 | + | + |
| 17 | + | + |
| 18 | + | + |
| 19 | + | + |
| 20 | + | + |
| 21 | + | + |
| 22 | + | + |
| 23 | + | + |
| 24 | + | + |
| 25 | + | + |
| 26 | + | + |
| 27 | + | + |
| 28 | + | + |
| 29 | + | + |

*Symbols used:
+: IC$_{50}$ ≤ 25 nM
++: 25 nM < IC$_{50}$ ≤ 100 nM
+++: 100 nM < IC$_{50}$ ≤ 1000 nM

Example B1: KMS.12.BM Cell Viability Assay

KMS.12.BM cell line (human myeloma) was purchased from JCRB (Osaka, Japan) and maintained in RPMI with 10% FBS culture medium. To measure the cytotoxic activity of the compounds through ATP quantitation, the KMS.12.BM cells are plated in the RPMI culture medium at 5000 cells/well/per 100 μL into a 96-well polystyrene clear black tissue culture plate (Greiner-bio-one through VWR, NJ), in the presence or absence of a concentration range of test compounds. After 3 days, 100 mL Cell Titer-GLO Luminescent (Promega, Madison, Wis.) cell culture agent is added to each well for 10 min. at room temperature to stabilize the luminescent signal. This determines the number of viable cells in culture based on quantitation of the ATP present, which signals the presence of metabolically active cells. Luminescence is measured with the Top Count 384 (Packard Bioscience through Perkin Elmer, Boston, Mass.). Compound inhibition is determined relative to cells cultured with no drug and the IC$_{50}$ reported as the compound concentration required for 50% cell death.

Compounds of the invention are considered to be active BET inhibitors if their IC$_{50}$ in the KMS.12.BM Cell Viability Assay is 2 μM or less. Examples 1-29 of the invention have been tested in the KMS.12.BM Cell Viability Assay and were found to be active BET inhibitors.

IC$_{50}$ data for the compounds of Examples 1 to 29 as determined by Assay B1 is presented in Table 4 (+ refers to IC$_{50}$≤100 nM; ++ refers to 100 nM<IC$_{50}$≤1000 nM; and +++ refers to 1000 nM<IC$_{50}$≤2000 nM).

TABLE 4

| Example No. | KMS cellular IC$_{50}$ (nM) |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |

Example C1

KMS.12.BM C-myc ELISA Assay

KMS.12.BM cell line (human myeloma) was purchased from JCRB (Osaka, Japan) and maintained in RPMI with 10% FBS culture medium. To measure the C-myc inhibitory activity of the compounds, the KMS.12.BM cells are plated in the RPMI culture medium at 75000 cells/well/per 200 μL into a 96-well flat bottom polystyrene tissue culture plate (Corning through VWR, NJ), in the presence or absence of a concentration range of test compounds. After 2 h, cells are pelleted and lysed with Cell Extraction Buffer (BioSource, Carlsbad, Calif.) in the presence of protease inhibitors (Life Technologies, Grand Island, N.Y. and Sigma, St Louis, Mo.). Clarified lyses are tested in a C-myc commercial ELISA (Life Technologies, Grand Island, N.Y.). Compound inhibition is determined relative to cells cultured with no drug and the IC$_{50}$ reported as the compound concentration required for 50% C-myc inhibition.

Compounds of the invention are considered to be active BET inhibitors if their IC$_{50}$ in the KMS.12.BM C-myc ELISA Assay is 5 μM or less. Examples 1-29 of the invention have been tested in the KMS.12.BM C-myc ELISA Assay and were found to be active BET inhibitors.

IC$_{50}$ data for the compounds of Examples 1 to 29 as determined by Assay C1 is presented in Table 5.

TABLE 5

| Example No. | KMS C-myc IC$_{50}$ (nM)* |
|---|---|
| 1 | + |
| 2 | + |
| 3 | + |
| 4 | + |
| 5 | + |
| 6 | + |

TABLE 5-continued

| Example No. | KMS C-myc IC$_{50}$ (nM)* |
|---|---|
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | ++ |
| 21 | + |
| 22 | + |
| 23 | ++ |
| 24 | + |
| 25 | + |
| 26 | + |
| 27 | + |
| 28 | ++ |
| 29 | + |

*Symbols used:
+: IC$_{50}$ ≤ 100 nM
++: 100 nM < IC$_{50}$ ≤ 1000 nM
+++: 1000 nM < IC$_{50}$ ≤ 5000 nM Various modifications of the invention, in addition to those described herein, will be apparent to those skilled in the art from the foregoing description. Such modifications are also intended to fall within the scope of the appended claims. Each reference cited in the present disclosure, including all patent, patent applications, and publications, is incorporated herein by reference in its entirety.

What is claimed is:

1. A compound which is:
(4S)-7-(3,5-dimethylisoxazol-4-yl)-2-[(3S)-4-isobutyryl-3-methylpiperazin-1-yl]-4-pyridin-2-yl-4,5-dihydroimidazo[1,5,4-de][1,4]benzoxazine;
or a pharmaceutically acceptable salt thereof.

2. A pharmaceutical composition comprising the compound of claim 1, or a pharmaceutically acceptable salt thereof, and at least one pharmaceutically acceptable carrier.

3. A method of treating cancer comprising administering to a patient in need of such treatment a therapeutically effective amount of the compound of claim 1, or a pharmaceutically acceptable salt thereof, wherein the cancer is adenocarcinoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell leukemia, T-cell lymphoma, testicular cancer, thyroid cancer, throat cancer, urogenital cancer, urothelial carcinoma, uterine cancer, vaginal cancer, or Wilms' tumor.

4. A method of treating an autoimmune or inflammatory disease comprising administering to a patient in need of such treatment a therapeutically effective amount of a compound of claim 1, or a pharmaceutically acceptable salt thereof, wherein the autoimmune or inflammatory disease is selected from allergy, allergic rhinitis, arthritis, asthma, chronic obstructive pulmonary disease, degenerative joint disease, dermatitis, organ rejection, eczema, hepatitis, inflammatory bowel disease, multiple sclerosis, myasthenia gravis, psoriasis, sepsis, sepsis syndrome, septic shock, systemic lupus erythematosus, tissue graft rejection, and type I diabetes.

5. A method of treating a viral infection comprising administering to a patient in need of such treatment a therapeutically effective amount of the compound of claim 1, or a pharmaceutically acceptable salt thereof.

6. The method of claim 5, wherein the viral infection is infection with adenovirus, Epstein-Barr virus, hepatitis B virus, hepatitis C virus, a herpes virus, human immunodeficiency virus, human papilloma virus or a pox virus.

* * * * *